US012709767B2

(12) United States Patent
Weitz et al.

(10) Patent No.: US 12,709,767 B2
(45) **Date of Patent: *Aug. 18, 2026**

(54) BARCODING SYSTEMS AND METHODS FOR GENE SEQUENCING AND OTHER APPLICATIONS

(71) Applicant: President and Fellows of Harvard College, Cambridge, MA (US)

(72) Inventors: David A. Weitz, Cambridge, MA (US); Huidan Zhang, Cambridge, MA (US); John Heyman, Cambridge, MA (US); Allon Moshe Klein, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 194 days.

This patent is subject to a terminal disclaimer.

(21) Appl. No.: 18/353,058

(22) Filed: Jul. 14, 2023

(65) Prior Publication Data

US 2024/0043893 A1 Feb. 8, 2024

Related U.S. Application Data

(63) Continuation of application No. 15/566,904, filed as application No. PCT/US2016/027734 on Apr. 15, 2016, now Pat. No. 11,746,367.

(60) Provisional application No. 62/149,361, filed on Apr. 17, 2015.

(51) Int. Cl.
*C12P 19/34* (2006.01)
*C12N 15/10* (2006.01)
*C12Q 1/6869* (2018.01)

(52) U.S. Cl.
CPC .......... *C12P 19/34* (2013.01); *C12N 15/1006* (2013.01); *C12N 15/1065* (2013.01); *C12N 15/1093* (2013.01); *C12Q 1/6869* (2013.01); *C12Q 2600/156* (2013.01)

(58) Field of Classification Search
CPC ............ C12N 15/1006; C12N 15/1065; C12N 15/1093; C12Q 1/6869
See application file for complete search history.

(56) References Cited

U.S. PATENT DOCUMENTS

| | | | |
|---|---|---|---|
| 5,750,346 | A | 5/1998 | Andre et al. |
| 6,013,445 | A | 1/2000 | Albrecht et al. |
| 6,054,278 | A | 4/2000 | Dodge et al. |
| 6,312,911 | B1 | 11/2001 | Bancroft et al. |
| 6,696,022 | B1 | 2/2004 | Chen et al. |
| 6,750,016 | B2 | 6/2004 | Mirkin et al. |
| 6,974,669 | B2 | 12/2005 | Mirkin et al. |
| 7,708,949 | B2 | 5/2010 | Stone et al. |
| 8,293,535 | B2 | 10/2012 | Farquar et al. |
| 8,337,778 | B2 | 12/2012 | Stone et al. |
| 8,592,150 | B2 | 11/2013 | Drmanac et al. |
| 8,765,485 | B2 | 7/2014 | Link et al. |
| 8,778,609 | B1 | 7/2014 | Umbarger |
| 8,829,171 | B2 | 9/2014 | Steemers et al. |
| 8,841,071 | B2 | 9/2014 | Link |
| 9,023,650 | B2 | 5/2015 | Farquar et al. |
| 9,388,465 | B2 | 7/2016 | Hindson et al. |
| 9,410,201 | B2 | 8/2016 | Hindson et al. |
| 9,567,631 | B2 | 2/2017 | Hindson et al. |
| 9,644,204 | B2 | 5/2017 | Hindson et al. |
| 9,689,024 | B2 | 6/2017 | Hindson et al. |
| 9,694,361 | B2 | 7/2017 | Bharadwaj et al. |
| 9,695,468 | B2 | 7/2017 | Hindson et al. |
| 9,701,998 | B2 | 7/2017 | Hindson et al. |
| 9,708,654 | B2 | 7/2017 | Hunicke-Smith et al. |

(Continued)

FOREIGN PATENT DOCUMENTS

| | | | |
|---|---|---|---|
| CN | 101946010.00 | A1 | 1/2011 |
| CN | 102439177 | A | 5/2012 |

(Continued)

OTHER PUBLICATIONS

European Office Action mailed Apr. 3, 2025 for Application No. EP 16780825.2.

Extended European Search Report for Application No. EP 13758373.8 mailed Nov. 24, 2015.

(Continued)

*Primary Examiner* — Sahana S Kaup

(74) *Attorney, Agent, or Firm* — Wolf, Greenfield & Sacks, P.C.

(57) ABSTRACT

The present invention generally relates to microfluidics and labeled nucleic acids. For example, certain aspects are generally directed to systems and methods for labeling nucleic acids within microfluidic droplets or other compartments, for instance, arising from a cell. In one set of embodiments, particles may be prepared containing oligonucleotides that can be used to determine target nucleic acids, e.g., attached to the surface of the particles. The oligonucleotides may include "barcodes" or unique sequences that can be used to distinguish nucleic acids in a droplet from those in another droplet, for instance, even after the nucleic acids are pooled together or removed from the droplets. Certain embodiments of the invention are generally directed to systems and methods for attaching additional or arbitrary sequences to the nucleic acids within microfluidic droplets or other compartments, e.g., recognition sequences that can be used to selectively determine or amplify a desired sequence suspected of being present within a droplet. Such systems may be useful, for example, for selective amplification in various applications, such as high-throughput sequencing applications.

13 Claims, 5 Drawing Sheets

Specification includes a Sequence Listing.

(56) References Cited

U.S. PATENT DOCUMENTS

| | | | |
|---|---|---|---|
| 10,596,541 | B2 | 3/2020 | Weitz et al. |
| 11,001,883 | B2 | 5/2021 | Rotem et al. |
| 11,047,003 | B2 | 6/2021 | Rotem et al. |
| 11,052,368 | B2 | 7/2021 | Weitz et al. |
| 11,746,367 | B2 | 9/2023 | Weitz et al. |
| 2002/0026046 | A1 | 2/2002 | Pasloske et al. |
| 2003/0082668 | A1 | 5/2003 | Tamai et al. |
| 2003/0152994 | A1 | 8/2003 | Woudenberg et al. |
| 2005/0266407 | A1 | 12/2005 | Chee et al. |
| 2006/0137434 | A1 | 6/2006 | Cohen et al. |
| 2006/0153924 | A1 | 7/2006 | Griffiths et al. |
| 2007/0000342 | A1 | 1/2007 | Link et al. |
| 2007/0031865 | A1 | 2/2007 | Willoughby |
| 2007/0052781 | A1 | 3/2007 | Fraden et al. |
| 2007/0077572 | A1 | 4/2007 | Tawfik et al. |
| 2007/0195127 | A1 | 8/2007 | Ahn et al. |
| 2008/0268450 | A1 | 10/2008 | Nam et al. |
| 2009/0098555 | A1 | 4/2009 | Roth et al. |
| 2009/0105959 | A1 | 4/2009 | Braverman et al. |
| 2009/0181375 | A1 | 7/2009 | Peter et al. |
| 2009/0181864 | A1 | 7/2009 | Chai et al. |
| 2009/0203063 | A1 | 8/2009 | Wheeler et al. |
| 2009/0208975 | A1 | 8/2009 | D'Costa et al. |
| 2010/0022414 | A1 | 1/2010 | Link et al. |
| 2010/0105052 | A1 | 4/2010 | Drmanac et al. |
| 2010/0120097 | A1 | 5/2010 | Aglyamova et al. |
| 2010/0136544 | A1 | 6/2010 | Agresti et al. |
| 2010/0216151 | A1 | 8/2010 | Lapidus et al. |
| 2010/0248237 | A1 | 9/2010 | Froehlich et al. |
| 2010/0261230 | A1 | 10/2010 | Liu et al. |
| 2010/0285975 | A1 | 11/2010 | Mathies et al. |
| 2010/0323348 | A1 | 12/2010 | Hamady et al. |
| 2010/0323361 | A1 | 12/2010 | Pugh et al. |
| 2011/0033854 | A1 | 2/2011 | Drmanac et al. |
| 2011/0267457 | A1 | 11/2011 | Agresti et al. |
| 2011/0275063 | A1 | 11/2011 | Weitz et al. |
| 2011/0281736 | A1 | 11/2011 | Drmanac et al. |
| 2011/0318786 | A1 | 12/2011 | Reichert et al. |
| 2012/0010091 | A1 | 1/2012 | Linnarson |
| 2012/0015822 | A1 | 1/2012 | Weitz et al. |
| 2012/0022094 | A1 | 1/2012 | Harris et al. |
| 2012/0028818 | A1 | 2/2012 | Öhman et al. |
| 2012/0058468 | A1 | 3/2012 | Mckeown |
| 2012/0122714 | A1 | 5/2012 | Samuels et al. |
| 2012/0132288 | A1 | 5/2012 | Weitz et al. |
| 2012/0157322 | A1 | 6/2012 | Myllykangas et al. |
| 2012/0196758 | A1 | 8/2012 | Klausing et al. |
| 2012/0211084 | A1 | 8/2012 | Weitz et al. |
| 2012/0220494 | A1* | 8/2012 | Samuels .............. C12Q 1/6806 506/26 |
| 2012/0309002 | A1 | 12/2012 | Link et al. |
| 2012/0322691 | A1 | 12/2012 | Sachidanandam et al. |
| 2013/0005585 | A1 | 1/2013 | Anderson et al. |
| 2013/0130919 | A1 | 5/2013 | Chen et al. |
| 2013/0165346 | A1 | 6/2013 | Wang et al. |
| 2013/0178369 | A1 | 7/2013 | Burns et al. |
| 2013/0219534 | A1 | 8/2013 | Wong et al. |
| 2013/0225418 | A1 | 8/2013 | Watson |
| 2013/0261019 | A1 | 10/2013 | Lin et al. |
| 2013/0261027 | A1 | 10/2013 | Li et al. |
| 2013/0274117 | A1 | 10/2013 | Church et al. |
| 2014/0057799 | A1 | 2/2014 | Johnson et al. |
| 2014/0094373 | A1* | 4/2014 | Zimmermann .... C12N 15/1089 506/1 |
| 2014/0141436 | A1 | 5/2014 | Erlich et al. |
| 2014/0194324 | A1 | 7/2014 | Gormley et al. |
| 2014/0200162 | A1 | 7/2014 | Saito et al. |
| 2014/0228255 | A1 | 8/2014 | Hindson et al. |
| 2014/0274729 | A1 | 9/2014 | Kurn et al. |
| 2014/0378345 | A1 | 12/2014 | Hindson et al. |
| 2015/0011432 | A1 | 1/2015 | Saxonov |
| 2015/0034163 | A1 | 2/2015 | Abate et al. |
| 2015/0051117 | A1 | 2/2015 | Church et al. |
| 2015/0057163 | A1 | 2/2015 | Rotem et al. |
| 2015/0298091 | A1 | 10/2015 | Weitz et al. |
| 2015/0329852 | A1 | 11/2015 | Nolan |
| 2015/0344938 | A1 | 12/2015 | Andersen et al. |
| 2016/0145683 | A1 | 5/2016 | Fan et al. |
| 2016/0194694 | A1 | 7/2016 | Andersen et al. |
| 2016/0312213 | A1 | 10/2016 | Rokhsar et al. |
| 2017/0028377 | A1 | 2/2017 | Bernstein et al. |
| 2017/0029813 | A1 | 2/2017 | Weitz et al. |
| 2018/0023133 | A1 | 1/2018 | Rotem et al. |
| 2018/0071705 | A1 | 3/2018 | Weitz et al. |
| 2018/0087078 | A1 | 3/2018 | Weitz et al. |
| 2018/0155777 | A1 | 6/2018 | Weitz et al. |
| 2018/0155778 | A1 | 6/2018 | Weitz et al. |
| 2018/0265922 | A1 | 9/2018 | Weitz et al. |
| 2018/0304222 | A1 | 10/2018 | Weitz et al. |
| 2018/0371540 | A1 | 12/2018 | Hindson et al. |
| 2019/0361010 | A1 | 11/2019 | Belhocine et al. |
| 2020/0123582 | A1 | 4/2020 | Tan et al. |
| 2021/0355535 | A1 | 11/2021 | Weitz et al. |
| 2021/0379555 | A1 | 12/2021 | Weitz et al. |

FOREIGN PATENT DOCUMENTS

| | | | | |
|---|---|---|---|---|
| CN | 103717749.00 | A | 4/2014 | |
| EP | 2 359 689 | A1 | 8/2011 | |
| EP | 2 977 455 | A1 | 1/2016 | |
| JP | 2007-503984 | A | 3/2007 | |
| JP | 2010-520749 | A | 6/2010 | |
| JP | 2010-193884 | A | 9/2010 | |
| JP | 2011-509075 | | 3/2011 | |
| JP | 2014-512826 | A | 5/2014 | |
| JP | 2015-528283 | A | 9/2015 | |
| JP | 2017-515469 | A | 6/2017 | |
| WO | WO 2004/002627 | A2 | 1/2004 | |
| WO | WO 2004091763 | A2 | 10/2004 | |
| WO | WO 2005021151 | A1 | 3/2005 | |
| WO | WO 2005062982 | A2 | 7/2005 | |
| WO | WO 2006096571 | A2 | 9/2006 | |
| WO | WO 2007089541 | A2 | 8/2007 | |
| WO | WO 2008000090 | A1 | 1/2008 | |
| WO | WO 2008109176 | A2 | 9/2008 | |
| WO | WO 2008127789 | A2 | 10/2008 | |
| WO | WO 2009011808 | A1 | 1/2009 | |
| WO | WO 2009015296 | A1 | 1/2009 | |
| WO | WO 2009085215 | A1 | 7/2009 | |
| WO | WO 2010025310 | A2 | 3/2010 | |
| WO | WO 2010033200 | A2 | 3/2010 | |
| WO | WO 2010080134 | A1 | 7/2010 | |
| WO | WO 2010151776 | A2 | 12/2010 | |
| WO | WO 2011056546 | A1 | 5/2011 | |
| WO | WO 2011140510 | A2 | 11/2011 | |
| WO | WO 2012003330 | A2 | 1/2012 | |
| WO | WO 2012016136 | A2 | 2/2012 | |
| WO | WO 2012019765 | A1 | 2/2012 | |
| WO | WO 2012048340 | A2 | 4/2012 | |
| WO | WO 2012048341 | A1 | 4/2012 | |
| WO | WO 2012083225 | A2 | 6/2012 | |
| WO | WO 2012/094642 | A2 | 7/2012 | |
| WO | WO 2012/112804 | A1 | 8/2012 | |
| WO | WO 2012/128717 | A1 | 9/2012 | |
| WO | WO 2012/149042 | A2 | 11/2012 | |
| WO | WO-2012162267 | A2 * | 11/2012 | ............. C12N 15/10 |
| WO | WO 2013/011611 | A1 | 1/2013 | |
| WO | WO 2013/116698 | A2 | 8/2013 | |
| WO | WO 2013/123125 | A1 | 8/2013 | |
| WO | WO 2013/134261 | A1 | 9/2013 | |
| WO | WO 2013/142389 | A1 | 9/2013 | |
| WO | WO 2013/188872 | A1 | 12/2013 | |
| WO | WO 2014/028537 | A | 2/2014 | |
| WO | WO 2014/047561 | A1 | 3/2014 | |
| WO | WO 2014/145555 | A1 | 9/2014 | |
| WO | WO-2014210353 | A2 * | 12/2014 | ........... C12Q 1/6813 |
| WO | WO 2015/031691 | A1 | 3/2015 | |
| WO | WO 2015/103339 | A1 | 7/2015 | |
| WO | WO 2015/160919 | A1 | 10/2015 | |
| WO | WO 2015/161177 | A1 | 10/2015 | |
| WO | WO 2015/164212 | A1 | 10/2015 | |
| WO | WO 2015/200541 | A1 | 12/2015 | |

(56) References Cited

FOREIGN PATENT DOCUMENTS

WO WO 2016/040476 A1 3/2016
WO WO 2016/168584 A1 10/2016

OTHER PUBLICATIONS

European Office Action for Application No. EP 13758373.8 mailed Nov. 18, 2016.
European Office Action for Application No. EP 13758373.8 mailed Oct. 12, 2017.
European Office Action for Application No. EP 3758373.8 mailed Apr. 24, 2018.
European Search Report for Application No. EP 17201280.9 mailed Feb. 12, 2018.
Extended European Search Report for Application No. EP 17201280.9 mailed May 23, 2018.
European Office Action mailed Oct. 9, 2019 for Application No. EP 17201280.9.
Extended European Search Report for Application No. EP 18215320.5 mailed Mar. 14, 2019.
European Office Action for Application No. EP 18215320.5 mailed Nov. 11, 2020.
European Office Action dated Aug. 11, 2021 for Application No. 18215320.5.
European Office Action dated Feb. 23, 2023 for Application No. 18215320.5.
International Search Report and Written Opinion for Application No. PCT/US2013/029123 mailed May 23, 2013.
International Preliminary Report on Patentability for Application No. PCT/US2013/029123 mailed Sep. 18, 2014.
Australian Examination Report mailed Sep. 11, 2020 for Application No. AU 2015247416.
Canadian Office Action mailed Apr. 19, 2021 for Application No. CA 2945794.
Canadian Office Action mailed Feb. 25, 2022 for Application No. CA 2945794.
Canadian Office Action mailed Dec. 8, 2022 for Application No. CA 2945794.
Chinese Office Action mailed Jan. 28, 2019 for Application No. 201580029304.3.
Extended European Search Report for Application No. EP 15780044.2 mailed Oct. 26, 2017.
European Communication mailed Sep. 4, 2018 for Application No. EP15780044.2.
Japanese Office Action mailed Apr. 2, 2019 for Application No. JP 2017-506636.
International Search Report and Written Opinion for Application No. PCT/US2015/026338 mailed Sep. 8, 2015.
International Preliminary Report on Patentability for Application No. PCT/US2015/026338 mailed Oct. 27, 2016.
Canadian Office Action mailed Mar. 3, 2022 for Application No. CA 2945798.
Canadian Office Action mailed Feb. 21, 2023 for Application No. CA 2945798.
Chinese Office Action mailed Nov. 29, 2018 for Application No. 201580029045.4.
Chinese Office Action mailed Jun. 5, 2020 for Application No. 201580029045.4.
Extended European Search Report for Application No. EP 15780364.4 mailed Oct. 23, 2017.
European Communication mailed Sep. 4, 2018 for Application No. EP15780364.4.
European Office Action for Application No. EP 15780364.4 mailed Aug. 29, 2019.
International Search Report and Written Opinion for Application No. PCT/US2015/026422 mailed Sep. 2, 2015.
International Preliminary Report on Patentability for Application No. PCT/US2015/026422 mailed Oct. 27, 2016.
Australian Examination Report mailed Sep. 25, 2018 for Application No. 2015250034.
Canadian Office Action mailed Apr. 1, 2021 for Application No. CA 2946144.
Canadian Office Action mailed Feb. 4, 2022 for Application No. CA 2946144.
Canadian Office Action mailed Jan. 31, 2023 for Application No. CA 2946144.
Chinese Office Action mailed Jun. 23, 2020 for Application No. 201580029081.0.
Chinese Office Action mailed Jan. 20, 2021 for Application No. 201580029081.0.
Chinese Office Action mailed Apr. 21, 2021 for Application No. CN 201580029081.0.
Extended European Search Report for Application No. EP 15783629.7 mailed Nov. 17, 2017.
European Office Communication mailed Jul. 6, 2018 for Application No. EP 15783629.7.
Extended European Search Report for Application No. EP 17198030.3 mailed Jan. 19, 2018.
European Office Action mailed Oct. 22, 2018 for Application No. 17198030.3.
European Office Action mailed Mar. 21, 2019 for Application No. 17198030.3.
Extended European Search Report mailed Jan. 21, 2019 for Application No. 18201501.6.
European Office Action mailed Oct. 1, 2019 for Application No. EP 18201501.6.
European Office Action mailed Mar. 10, 2020 for Application No. EP18201501.6.
European Office Action mailed Oct. 21, 2020 for Application No. 18201501.6.
European Office Action mailed Mar. 15, 2021 for Application No. 18201501.6.
Japanese Office Action mailed Mar. 19, 2019 for Application No. JP 2016-564093.
Japanese Office Action mailed Nov. 26, 2019 for Application No. JP 2016-564093.
Japanese Office Action mailed Aug. 4, 2020 for Application No. JP 2016-564093.
International Search Report and Written Opinion for Application No. PCT/US2015/026443, mailed Jul. 27, 2015.
International Preliminary Report on Patentability for Application No. PCT/US2015/026443 mailed Nov. 3, 2016.
Australian Office Action mailed Jun. 10, 2021 for Application No. AU 2016248995.
Chinese Office Action mailed Apr. 26, 2020 for Application No. CN 201680031721.6.
Chinese Office Action mailed Feb. 3, 2021 for Application No. 201680031721.6.
Chinese Office Action mailed Jul. 23, 2021 for Application No. 201680031721.6.
Extended European Search Report mailed Aug. 1, 2018 for Application No. 16780825.
European Office Action mailed Dec. 16, 2019 for Application No. EP 16780825.2.
European Office Action mailed Aug. 21, 2020 for Application No. EP 16780825.2.
European Office Action dated Jun. 1, 2021 for Application No. 16780825.2.
European Office Action dated Jan. 17, 2022 for Application No. 16780825.2.
Japanese Office Action mailed Mar. 31, 2020 for Application No. 2017-554339.
Japanese Office Action mailed Mar. 3, 2021 for Application No. 2017-554339.
International Search Report and Written Opinion for Application No. PCT/US2016/027734 mailed Jul. 14, 2016.
International Preliminary Report on Patentability for Application No. PCT/US2016/027734 mailed Oct. 26, 2017.
International Search Report and Written Opinion for Application No. PCT/US2017/043660 mailed Nov. 6, 2017.
International Preliminary Report on Patentability mailed Feb. 7, 2019 for Application No. PCT/US2017/043660.

(56) References Cited

OTHER PUBLICATIONS

Office Action mailed Sep. 24, 2015 for U.S. Appl. No. 14/734,903.
Office Action mailed Feb. 1, 2016 for U.S. Appl. No. 14/734,903.
Advisory Action mailed May 19, 2016 for U.S. Appl. No. 14/734,903.
Office Action mailed Jun. 2, 2016 for U.S. Appl. No. 14/478,672.
Office Action mailed Oct. 7, 2016 for U.S. Appl. No. 14/734,903.
Office Action mailed Dec. 29, 2016 for U.S. Appl. No. 14/478,672.
Office Action mailed Apr. 14, 2017 for U.S. Appl. No. 14/734,903.
Notice of Allowance mailed Jun. 14, 2017 for U.S. Appl. No. 14/478,672.
Advisory Action mailed Aug. 2, 2017 for U.S. Appl. No. 14/734,903.
Office Action mailed Sep. 12, 2017 for U.S. Appl. No. 14/734,903.
Office Action mailed Oct. 6, 2017 for U.S. Appl. No. 15/303,893.
Office Action mailed Oct. 6, 2017 for U.S. Appl. No. 15/303,874.
Office Action mailed Nov. 17, 2017 for U.S. Appl. No. 14/478,672.
Office Action mailed Apr. 30, 2018 for U.S. Appl. No. 15/723,490.
Office Action mailed May 17, 2018 for U.S. Appl. No. 15/303,893.
Office Action mailed Jun. 5, 2018 for U.S. Appl. No. 14/478,672.
Final Office Action mailed Jun. 22, 2018 for U.S. Appl. No. 15/303,874.
Office Action mailed Jul. 5, 2018 for U.S. Appl. No. 14/734,903.
Office Action mailed Nov. 14, 2018 for U.S. Appl. No. 15/723,490.
Office Action mailed Dec. 6, 2018 for U.S. Appl. No. 14/478,672.
Office Action mailed Feb. 12, 2019 for U.S. Appl. No. 14/734,903.
Advisory Action mailed Feb. 14, 2019 for U.S. Appl. No. 15/723,490.
Office Action mailed Apr. 29, 2019 for U.S. Appl. No. 15/303,874.
Office Action mailed May 1, 2019 for U.S. Appl. No. 15/723,490.
Office Action mailed May 6, 2019 for U.S. Appl. No. 15/303,893.
Office Action mailed May 13, 2019 for U.S. Appl. No. 15/670,929.
Office Action mailed Aug. 6, 2019 for U.S. Appl. No. 14/734,903.
Office Action mailed Aug. 29, 2019 for U.S. Appl. No. 15/556,904.
Office Action mailed Oct. 30, 2019 for U.S. Appl. No. 15/670,929.
Office Action mailed Nov. 22, 2019 for U.S. Appl. No. 15/303,874.
Office Action mailed Feb. 4, 2020 for U.S. Appl. No. 14/734,903.
Office Action mailed Feb. 20, 2020 for U.S. Appl. No. 15/303,893.
Office Action mailed Mar. 19, 2020 for U.S. Appl. No. 15/836,520.
Office Action Mailed Apr. 21, 2020 for U.S. Appl. No. 15/566,904.
Office Action mailed Jun. 1, 2020 for U.S. Appl. No. 15/991,600.
Office Action mailed Jul. 17, 2020 for U.S. Appl. No. 15/965,452.
Final Office Action mailed Jul. 22, 2020 for U.S. Appl. No. 15/303,874.
Office Action mailed Nov. 5, 2020 for U.S. Appl. No. 15/836,520.
Office Action mailed Nov. 13, 2020 for U.S. Appl. No. 14/734,903.
Office Action Mailed Mar. 10, 2021 for U.S. Appl. No. 15/566,904.
Office Action Mailed Jun. 24, 2021 for U.S. Appl. No. 15/566,904.
[No Author Listed] Single-Cell Whole Transcriptome Profiling With the SOLiD System. AB Applied Biosystems. Apr. 2009 Publication 139AP16-01: 6 pages.
Adli et al., Genome-wide chromatin maps derived from limited numbers of hematopoietic progenitors. Nat Methods. Aug. 2010;7(8):615-8.
Barbazuk et al., SNP discovery via 454 transcriptome sequencing. Plant J. Sep. 2007;51(5):910-8. Epub Jul. 27, 2007.
Binladen et al., The use of coded PCR primers enables high-throughput sequencing of multiple homolog amplification products by 454 parallel sequencing. PLoS One. Feb. 14, 2007;2(2):e197.
Brouzes et al., Droplet microfluidic technology for single-cell high-throughput screening. Proc Natl Acad Sci U S A. Aug. 25, 2009;106(34):14195-200. doi: 10.1073/pnas.0903542106. Epub Jul. 15, 2009.
Buermans et al., New methods for next generation sequencing based microRNA expression profiling. BMC Genomics. Dec. 20, 2010;11:716.
Cheng et al., Anisotropic colloidal crystal particles from microfluidics. J Colloid Interface Sci. 2014;421:64-70.
Clausell-Tormos et al., Droplet-based microfluidic platforms for the encapsulation and screening of Mammalian cells and multicellular organisms. Chem Biol. May 2008;15(5):427-37. doi: 1016/j.chembiol. 2008.04.004. Erratum in: Chem Biol.Aug. 25, 2008;15(8):875.
Cloonan et al. Stem cell transcriptome profiling via massive-scale mRNA sequencing. Nat Methods. Jul. 2008;5(7):613-9. doi: 10.1038/nmeth.1223. Epub May 30, 2008.
Craig et al., Identification of genetic variants using bar-coded multiplexed sequencing. Nat Methods. Oct. 2008;5(10):887-93.
Dutchen, Beyond average. Harvard Medical School News. May 21, 2015. Accessed online May 28, 2015 at http://hms.harvard.edu/news/beyond-average. 6 pages.
Eastburn Ultrahigh-throughput Mammalian single-cell reverse-transcriptase polymerase chain reaction in microfluidic drops. Anal Chem. Aug. 20, 2013;85(16):8016-21. doi: 10.1021/ac402057q. Epub Aug. 8, 2013. PubMed PMID: 23885761.
Fan et al., Expression profiling. Combinatorial labeling of single cells for gene expression cytometry. Science. Feb. 6, 2015;347(6222): 1258367. doi: 10. 1 126/science.1258367.
Guo et al., Droplet microfluidics for high-throughput biological assays. Lab Chip. Jun. 21, 2012;12(12):2146-55. doi: 10.1039/c2lc21147e. Epub Feb. 9, 2012.
Guo et al., Resolution of cell fate decisions revealed by single-cell gene expression analysis from zygote to blastocyst. Dev Cell. Apr. 20, 2010;18(4):675-85.
Hamady et al., Error-correcting barcoded primers for pyrosequencing hundreds of samples in multiplex. Nat Methods. Mar. 2008;5(3):235-7.
Heuze et al., Molecular analysis of a pro-T cell clone transformed by Abelson-murine leukemia virus, displaying progressive gamma delta T cell receptor gene rearrangement and surface expression. Eur J Immunol. Aug. 1992;22(8):2077-84.
Hug et al., A chromatin immunoprecipitation screen reveals protein kinase Cbeta as a direct RUNX1 target gene. J Biol Chem. Jan. 9, 2004;279(2):825-30. Epub Oct. 15, 2003.
Islam et al. Characterization of the single-cell transcriptional landscape by highly multiplex RNA-seq.Genome Research.2011.(21)1160-1167.
Islam et al., Quantitative single-cell RNA-seq with unique molecular identifiers. Nat Methods. Feb. 2014;11(2):163-6. doi:10.1038/nmeth.2772. Epub Dec. 22, 2013.
Jaitin et al., Massively parallel single-cell RNA-seq for marker-free decomposition of tissues into cell types. Science. Feb. 14, 2014;343(6172):776-9. doi: 10. 1 126/science.1247651.
Kalisky et al. Single-cell genomics. Nat Methods. Apr. 2011;8(4):311-4. doi: 10.1038/nmeth0411-311.
Karow, Harvard groups develop fast, inexpensive droplet methods for RNA-seq of thousands of single cells. GenomeWeb. May 21, 2015. Accessed online May 27, 2015 at https ://www. genome web .com/sequencing-technology /harvard-groups-develop-fast-inexpensivedroplet-methods-rna-seq-thousands. 4 pages.
Kato, RNA fingerprinting by molecular indexing. Nucleic Acids Res. Jan. 15, 1996;24(2):394-5.
Klein et al. Comparative genomic hybridization, loss of heterozygosity, and DNA sequence analysis of single cells. Proc Natl Acad Sci U S A. Apr. 13, 1999;96(8):4494-9.
Klein et al., Droplet barcoding for single-cell transcriptomics applied to embryonic stem cells. Cell. May 22, 2015;161(5):1187-201. doi:10.1016/j.cell.2015.04.044.
Koster et al., Drop-based microfluidic devices for encapsulation of single cells. Lab Chip. 2008; 8:1110-1115.
Kumaresan et al., High-Throughput Single Copy DNA Amplification and Cell Analysis in Engineered Nanoliter Droplets. Anal Chem. May 15, 2008;80(10):3522-9.
Lau et al.,An abundant class of tiny RNAs with probable regulatory roles in Caenorhabditis elegans. Science. Oct. 26, 2001;294(5543):858-62.
Li et al., Sequence-specific label-free DNA sensors based on silicon nanowires. Nano Lett Feb. 4, 2004(2): 245-7.
Li et al., The Sequence Alignment/Map format and SAMtools. Bioinformatics. Aug. 15, 2009;25(16):2078-9.
Lu et al., Construction of small RNA cDNA libraries for deep sequencing. Methods. 2007;43(2):110-117.
Macosko et al., Highly parallel genome-wide expression profiling of individual cells using nanoliter droplets. Cell. May 2015;161:1202-1214.

(56) References Cited

OTHER PUBLICATIONS

Margulies et al., Genome sequencing in microfabricated high-density picolitre reactors. Nature. Sep. 15, 2005;437(7057):376-80. Epub Jul. 31, 2005.
Mazutis et al., Single-cell analysis and sorting using droplet-based microfluidics. Nat Protoc. May 2013;8(5):870-91. doi: 10.1038/nprot.2013.046. Epub Apr. 4, 2013.
Meyer et al., Illumina sequencing library preparation for highly multiplexed target capture and sequencing. Cold Spring Harb Protoc. Jun. 2010;2010(6):pdb.prot5448.
Meyer et al., Parallel tagged sequencing on the 454 platform. Nat Protoc. 2008;3(2):267-278.
Meyer et al., Targeted high-throughput sequencing of tagged nucleic acid samples. Nucleic Acids Res. ePub Aug. 1, 2007; 35(15):e97. 1-97.6.
Moreau et al.,Chronological changes in microRNA expression in the developing human brain. PLoS One. Apr. 16, 2013;8(4):e60480.
Ng et al., Multiplex sequencing of paired-end ditags (MS-PET): a strategy for the ultra-high-throughput analysis of transcriptomes and genomes. Nucleic Acids Res. Jul. 13, 2006;34(12):e84.
Nielsen et al., DeepSAGE—digital transcriptomics with high sensitivity, simple experimental protocol and multiplexing of samples. Nucleic Acids Res. 2006;34(19):e133. Epub Oct. 5, 2006.
Novak et al., Single-cell multiplex gene detection and sequencing with microfluidically generated agarose emulsions. Angew Chem Int Ed Engl. Jan. 10, 2011;50(2):390-5. doi: 10.1002/anie.201006089.
Okochi et al. Droplet-based gene expression analysis using a device with magnetic force-based-droplet-handling system. J of Bioscience and Bioengeneering.2010.(109)193-197.
O'Neill et al. Epigenetic characterization of the early embryo with a chromatin immunoprecipitation protocol applicable to small cell populations. Nat Genet. Jul. 2006;38(7):835-41. Epub Jun. 11, 2006.
O'Neill et al., Immunoprecipitation of native chromatin: NChIP. Methods. Sep. 2003;31(1):76-82.
Park et al., ChIP-seq: Advantages and challenges of a maturing technology. Nat Rev Genetics. Oct. 1, 2009; 10(10):669-680.
Rizzo et al., Standardized collection of MNase-seq experiments enables unbiased dataset comparisons. BMC Mol Biol. May 6, 2012;13:15.
Ross et al., Reverse transcription with random pentadecamer primers improves the detection limit of a quantitative PCR assay for BCR-ABL transcripts in chronic myeloid leukemia: implications for defining sensitivity in minimal residual disease. Clin Chem. Sep. 2008;54(9):1568-71.
Rotem et al. Single-cell ChIP-seq reveals cell subpopulations defined by chromatin state. Nature Biotechnology. 2015. (33)1165-1175.
Rotem et al., High-Throughput Single-Cell Labeling (Hi-SCL) for RNA-Seq Using Drop-Based Microfluidics. PLoS One. May 22, 2015;10(5):e0116328. doi:10.1371/journal.pone.0116328. eCollection 2015.
Rothberg et al., The development and impact of 454 sequencing. Nat Biotechnol. 2008;26(10):1117-1124.
Saha et al., Using the transcriptome to annotate the genome. Nat Biotechnol. May 2002;20(5):508-12.
Schones et al., Dynamic regulation of nucleosome positioning in the human genome. Cell. Mar. 7, 2008; 132(5):887-898.
Shi et al., Poly(T) adaptor RT-PCR. Methods Mol Biol. 2012;822:53-66.
Sokoloff, Effects of Capillary Forces on a Hydrogel Sphere Pressed against a Surface. Langmuir. Jan. 12, 2016;32(1):135-9. doi: 10.1021/acs.langmuir.5b04012. Epub Dec. 24, 2015.
Tang et al., mRNA-Seq whole-transcriptome analysis of a single cell. Nat Methods. May 2009;6(5):377-82.
Tang et al.RNA-Seq analysis to capture the transcriptome landscape of a single cell. Nat Protoc. Mar. 2010;5(3):516-35. doi: 10.1038/nprot.2009.236. Epub Feb. 25, 2010.
Teh et al., Droplet microfluidics. Lab Chip. Feb. 2008;8(2):198-220. doi: 10.1039/b715524g. Epub Jan. 11, 2008.
Tewhey et al., Microdroplet-based PCR enrichment for large-scale targeted sequencing. Nat Biotechnol. Nov. 2009;27(11):1025-31. doi: 10.1038/nbt.1583.
Van Nieuwerburgh et al., Quantitative bias in Illumina TruSeq and a novel post amplification barcoding strategy for multiplexed DNA and small RNA deep sequencing. PLoS One. 2011;6(10):e26969.
Velculescu et al., Serial analysis of gene expression. Science. Oct. 20, 1995;270(5235):484-7.
Vigneault et al. Efficient microRNA capture and bar-coding via enzymatic oligonucleotide adenylation. Nature Methods.2008.(5):777-779.
Wal et al., Genome-wide mapping of nucleosome positions in yeast using high-resolution MNase ChIP-Seq. Methods Enzymol. 2012;513:233-50.
Wang et al., Novel thermosensitive hydrogel injection inhibits post-infarct ventricle remodelling. Eur J Heart Fail. Jan. 2009;11(1):14-19. doi: 10.1093/eurjhf/hfn009.
Weber et al., Chromosome-wide and promoter-specific analyses identify sites of differential DNA methylation in normal and transformed human cells. Nat Genet. Aug. 2005;37(8):853-62. Epub Jul. 10, 2005.
Wei et al., A global map of p53 transcription-factor binding sites in the human genome. Cell. Jan. 13, 2006;124(1):207-19.
Weinman et al., Isolating human transcription factor targets by coupling chromatin immunoprecipitation and CpG island microarray analysis. Genes Dev. Jan. 15, 2002; 16(2): 235-244. doi: 10.1101/gad.943102.
Zeng et al., High-Performance Single Cell Genetic Analysis Using Microfluidic Emulsion Generator Arrays. Anal Chem. Apr. 15, 2010;82(8):3183-90.
Zhang et al., A surface topography assisted droplet manipulation platform for biomarker detection and pathogen identification. Lab Chip. Feb. 7, 2011;11(3):398-406.
Zhang et al., High-resolution genome-wide mapping of the primary structure of chromatin. Cell. Jan. 21, 2011;144(2):175-86.
Zhang et al., Modeling ChIP sequencing in silicon with applications. PLoS Comput Biol. Aug. 22, 2008;4(8):e1000158. doi: 10.1371/journal.pcbi.1000158.
Zheng et al., Titration-free massively parallel pyrosequencing using trace amounts of starting material. Nucleic Acids Res. Jul. 2010;38(13):e137.
Zilionis et al., Single-cell barcoding and sequencing using droplet microfluidics. Nat Protoc. Jan. 2017;12(1):44-73. doi: 10.1038/nprot.2016.154. Epub Dec. 8, 2016.
European Office Action for EP 18215320.5, mailed Nov. 22, 2024.
Chinese Office Action mailed Dec. 2, 2025 for Application No. CN 201680031721.6.

* cited by examiner

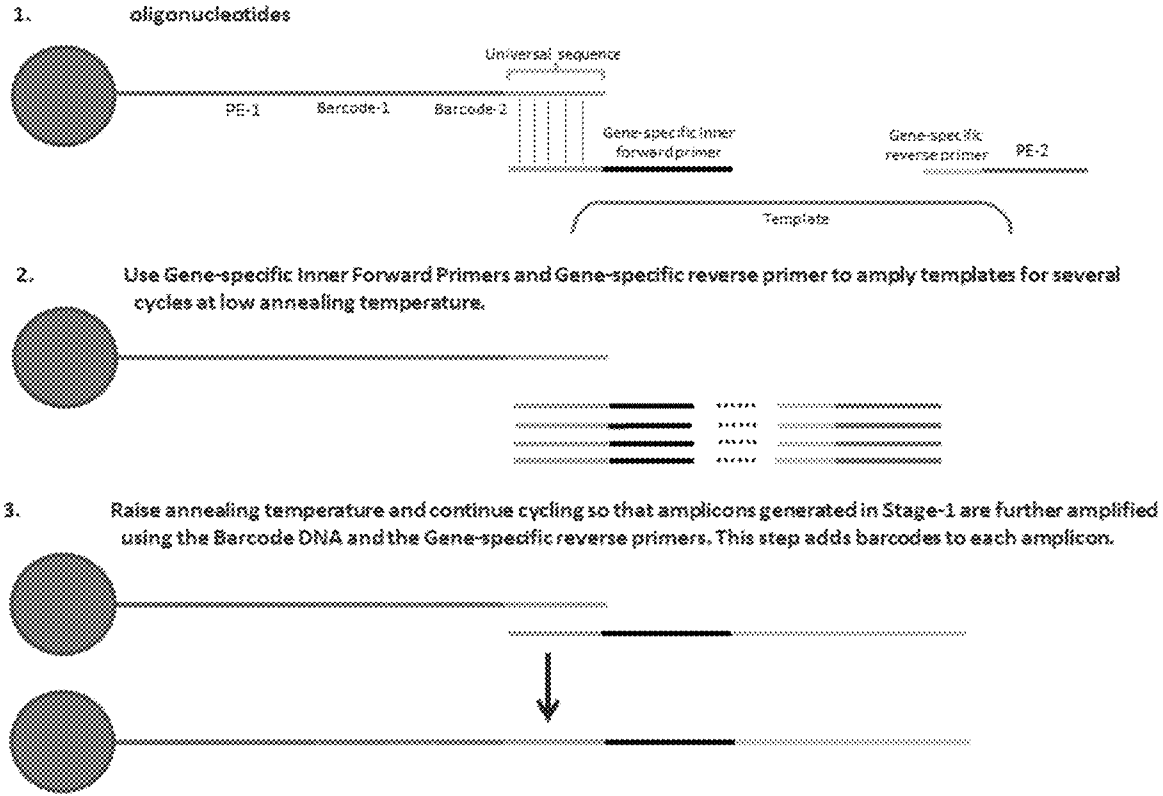

| | | |
|---|---|---|
| PE-1 | ACACTCTTTCCCTACACGACGCTCTTCCGATCT | SEQ ID NO: 1 |
| PE-2 | GTCTCGGCATTCCTGCTGAAC | SEQ ID NO: 2 |
| Universal primer | GCCTCTGTTCGTCTCG | SEQ ID NO: 3 |
| Gene-specific primer-F (example) | GCCTCTGTTCGTCTCG TAGAGGCAGTCATCGCAGTG | SEQ ID NO: 4 |
| Gene-specific primer-R (example) | GTCTCGGCATTCCTGCTGAAC GACCTACCAATCCCATTCCTT | SEQ ID NO: 5 |
| Barcode-1 (example) | AAACAAAC | |
| Barcode-2 (example) | TCGGTCATTCA | SEQ ID NO: 6 |

Figure 1A

| | | |
|---|---|---|
| PE-1 | Same as Fig.1 | |
| PE-2 | Same as Fig.1 | |
| Universal primer | TCGGCAGCGTCAGATGTGTATAAGAGACAGT | SEQ ID NO: 7 |
| Complementary sequence | CTGTCTCTTATACACATCTGACGCTGCCGA | SEQ ID NO: 8 |
| Gene-specific primer-F (example) | T*AGAGGCAGTCATCGCAGTG | SEQ ID NO: 9 |
| Gene-specific primer-R (example) | Same as Fig.1 | |
| Barcode-1 (example) | Same as Fig.1 | |
| Barcode-2 (example) | Same as Fig.1 | |

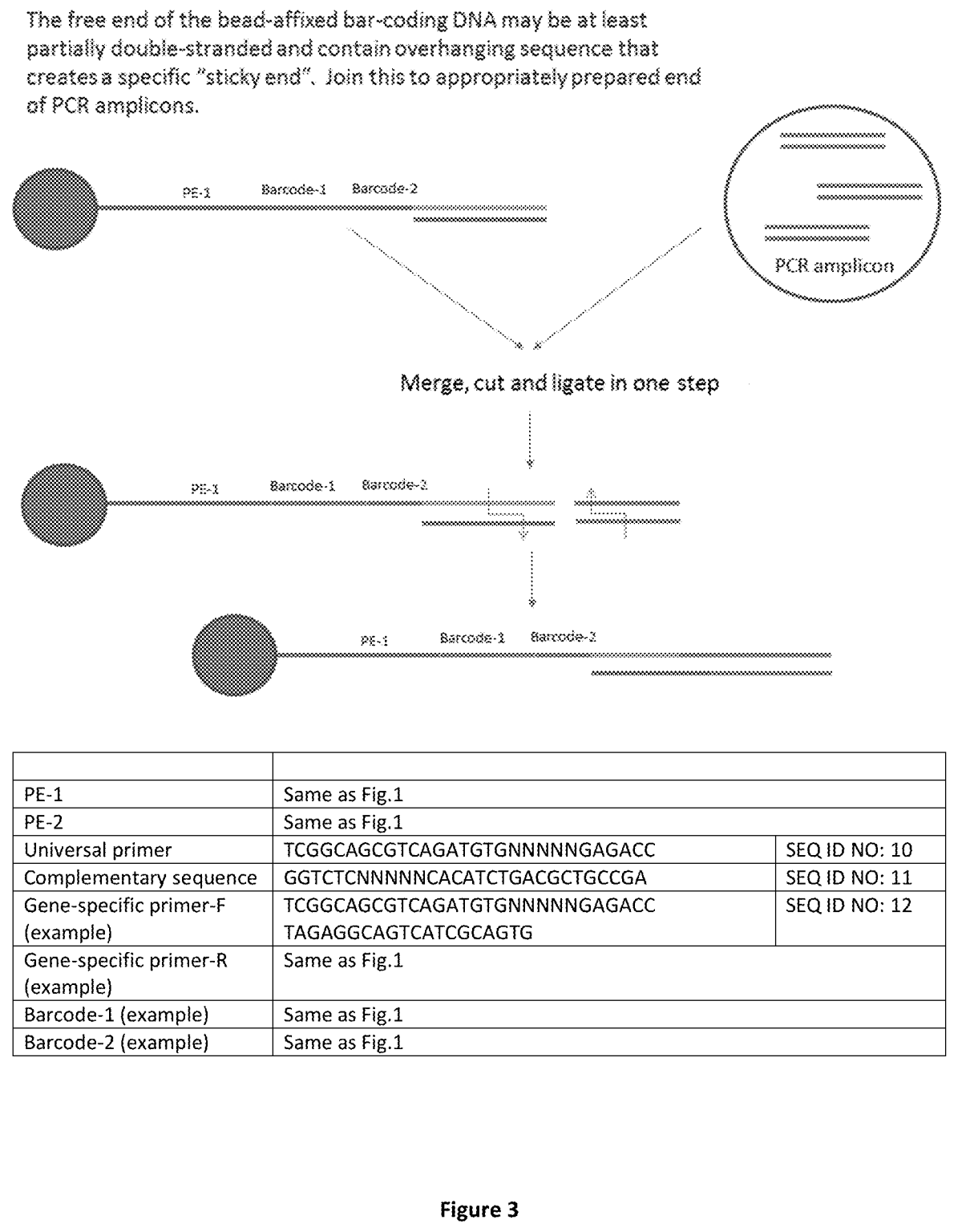

The free end of the bead-affixed bar-coding DNA may be at least partially double-stranded and contain overhanging sequence that creates a specific "sticky end". Join this to appropriately prepared end of PCR amplicons.

PE-1 Barcode-1 Barcode-2

PCR amplicon

Merge, cut and ligate in one step

PE-1 Barcode-1 Barcode-2

PE-1 Barcode-1 Barcode-2

| | | |
|---|---|---|
| PE-1 | Same as Fig.1 | |
| PE-2 | Same as Fig.1 | |
| Universal primer | TCGGCAGCGTCAGATGTGNNNNNGAGACC | SEQ ID NO: 10 |
| Complementary sequence | GGTCTCNNNNNCACATCTGACGCTGCCGA | SEQ ID NO: 11 |
| Gene-specific primer-F (example) | TCGGCAGCGTCAGATGTGNNNNNGAGACC TAGAGGCAGTCATCGCAGTG | SEQ ID NO: 12 |
| Gene-specific primer-R (example) | Same as Fig.1 | |
| Barcode-1 (example) | Same as Fig.1 | |
| Barcode-2 (example) | Same as Fig.1 | |

Figure 3

SEQUENCE LISTING

```
Sequence total quantity: 13
SEQ ID NO: 1            moltype = DNA  length = 33
FEATURE                 Location/Qualifiers
misc_feature            1..33
                        note = Synthetic Polynucleotide
source                  1..33
                        mol_type = other DNA
                        organism = synthetic construct
SEQUENCE: 1
acactctttc cctacacgac gctcttccga tct                              33

SEQ ID NO: 2            moltype = DNA  length = 21
FEATURE                 Location/Qualifiers
misc_feature            1..21
                        note = Synthetic Polynucleotide
source                  1..21
                        mol_type = other DNA
                        organism = synthetic construct
SEQUENCE: 2
gtctcggcat tcctgctgaa c                                           21

SEQ ID NO: 3            moltype = DNA  length = 16
FEATURE                 Location/Qualifiers
misc_feature            1..16
                        note = Synthetic Polynucleotide
source                  1..16
                        mol_type = other DNA
                        organism = synthetic construct
SEQUENCE: 3
gcctctgttc gtctcg                                                 16

SEQ ID NO: 4            moltype = DNA  length = 36
FEATURE                 Location/Qualifiers
misc_feature            1..36
                        note = Synthetic Polynucleotide
source                  1..36
                        mol_type = other DNA
                        organism = synthetic construct
SEQUENCE: 4
gcctctgttc gtctcgtaga ggcagtcatc gcagtg                           36

SEQ ID NO: 5            moltype = DNA  length = 42
FEATURE                 Location/Qualifiers
misc_feature            1..42
                        note = Synthetic Polynucleotide
source                  1..42
                        mol_type = other DNA
                        organism = synthetic construct
SEQUENCE: 5
gtctcggcat tcctgctgaa cgacctacca atcccattcc tt                    42

SEQ ID NO: 6            moltype = DNA  length = 11
FEATURE                 Location/Qualifiers
misc_feature            1..11
                        note = Synthetic Polynucleotide
source                  1..11
                        mol_type = other DNA
                        organism = synthetic construct
SEQUENCE: 6
tcggtcattc a                                                      11

SEQ ID NO: 7            moltype = DNA  length = 31
```

```
FEATURE                 Location/Qualifiers
misc_feature            1..31
                        note = Synthetic Polynucleotide
source                  1..31
                        mol_type = other DNA
                        organism = synthetic construct
SEQUENCE: 7
tcggcagcgt cagatgtgta taagagacag t                                31

SEQ ID NO: 8            moltype = DNA  length = 30
FEATURE                 Location/Qualifiers
misc_feature            1..30
                        note = Synthetic Polynucleotide
source                  1..30
                        mol_type = other DNA
                        organism = synthetic construct
SEQUENCE: 8
ctgtctctta tacacatctg acgctgccga                                  30

SEQ ID NO: 9            moltype = DNA  length = 20
FEATURE                 Location/Qualifiers
misc_feature            1..20
                        note = Synthetic Polynucleotide
misc_feature            1..2
                        note = Modified by phosphorothioate bond
source                  1..20
                        mol_type = other DNA
                        organism = synthetic construct
SEQUENCE: 9
tagaggcagt catcgcagtg                                             20

SEQ ID NO: 10           moltype = DNA  length = 29
FEATURE                 Location/Qualifiers
misc_feature            1..29
                        note = Synthetic Polynucleotide
misc_difference         19..23
                        note = n is a, c, g, or t
source                  1..29
                        mol_type = other DNA
                        organism = synthetic construct
SEQUENCE: 10
tcggcagcgt cagatgtgnn nnngagacc                                   29

SEQ ID NO: 11           moltype = DNA  length = 29
FEATURE                 Location/Qualifiers
misc_feature            1..29
                        note = Synthetic Polynucleotide
misc_difference         7..11
                        note = n is a, c, g, or t
source                  1..29
                        mol_type = other DNA
                        organism = synthetic construct
SEQUENCE: 11
ggtctcnnnn ncacatctga cgctgccga                                   29

SEQ ID NO: 12           moltype = DNA  length = 49
FEATURE                 Location/Qualifiers
misc_feature            1..49
                        note = Synthetic Polynucleotide
misc_difference         19..23
                        note = n is a, c, g, or t
source                  1..49
                        mol_type = other DNA
                        organism = synthetic construct
SEQUENCE: 12
tcggcagcgt cagatgtgnn nnngagacct agaggcagtc atcgcagtg             49

SEQ ID NO: 13           moltype = DNA  length = 64
FEATURE                 Location/Qualifiers
misc_feature            1..64
                        note = Synthetic Polynucleotide
source                  1..64
                        mol_type = other DNA
                        organism = synthetic construct
SEQUENCE: 13
cgatgacgta atacgactca ctatagggat accaccatgg ctctttccct acacgacgct  60
cttc                                                              64
```

BARCODING SYSTEMS AND METHODS FOR GENE SEQUENCING AND OTHER APPLICATIONS

RELATED APPLICATIONS

This application is a continuation of U.S. patent application Ser. No. 15/566,904, filed Oct. 16, 2017, which is a national stage filing under 35 U.S.C. § 371 of International Application No. PCT/US2016/027734, filed Apr. 15, 2016 entitled "Barcoding Systems and Methods For Gene Sequencing and Other Applications," by Weitz et al., which claims the benefit of U.S. Provisional Patent Application Ser. No. 62/149,361, filed Apr. 17, 2015, entitled "Barcoding Systems and Methods For Gene Sequencing and Other Applications," by Weitz, et al., each of which is incorporated herein by reference.

GOVERNMENT FUNDING

This invention was made with government support under HL120839 awarded by National Institutes of Health (NIH) and under 1310266 and 1420570 awarded by National Science Foundation (NSF). The government has certain rights in the invention.

REFERENCE TO AN ELECTRONIC SEQUENCE LISTING

The contents of the electronic sequence listing (H049870542US02-SEQ-TC.xml; Size: 19,250 bytes; and Date of Creation: Jul. 14, 2023) is herein incorporated by reference in its entirety.

FIELD

The present invention generally relates to microfluidics and labeled nucleic acids.

BACKGROUND

With the development of high-throughput sequencing technology, researchers have generated large amounts of genomic and epigenetic data. Disease-related genes have been extracted from patients and sequence information is used for clinical diagnosis and treatment.

High-throughput sequencing generally relies on performing a huge number of individual reactions, giving a few hundred bases of nucleic acid sequence. For example, a single "run" of an Illumina HiSeq sequencer (HiSeq 2500 Rapid Run Mode) takes 27 hours, generates ~1.2 billion paired end reads (reactions), giving ~150 bases of sequence. For many experiments, this massive amount of sequence information is much more than required for a single sample.

Thus, what would be desired, at least with respect to this problem, is the ability to tag ("barcode") samples prior to sequencing, so that many samples can be analyzed in a single sequencing run. An example is single-cell transcription analysis. A researcher may want to analyze the expression levels of several hundred genes for several hundred cells. This can be performed in a single HiSeq run if the RNA from individual cells are genetically tagged (barcoded) prior to sequencing.

SUMMARY

The present invention generally relates to microfluidics and labeled nucleic acids. The subject matter of the present invention involves, in some cases, interrelated products, alternative solutions to a particular problem, and/or a plurality of different uses of one or more systems and/or articles.

In one aspect, the present invention is generally directed to a method. In one set of embodiments, the method includes acts of providing a plurality of droplets comprising particles such that at least about 90% of the droplets contains one particle or no particle, the particles comprising oligonucleotides, and attaching a nucleic acid sequence to the oligonucleotides. In some cases, the oligonucleotides comprise a barcode sequence first barcode selected from a pre-defined pool of first barcodes and a second barcode selected from a pre-defined pool of second barcodes, e.g., such that substantially each of the particles comprises distinguishable barcode sequences.

The method, in accordance with another set of embodiments, includes providing a plurality of droplets comprising particles such that at least about 90% of the droplets contains one particle or no particles, the particles comprising oligonucleotides, the oligonucleotides comprising a barcode sequence first barcode selected from a pre-defined pool of first barcodes, a second barcode selected from a pre-defined pool of second barcodes, and an adapter sequence, such that substantially each of the particles comprises distinguishable barcode sequences; exposing the adapter sequence to a sequence comprising a complementary adapter sequence and a primer; exposing the primer to a nucleic acid sequence comprising a target of the primer; and applying amplification to produce an oligonucleotide comprising the first barcode, the second barcode, and the nucleic acid sequence.

In yet another set of embodiments, the method comprises providing a plurality of particles having attached thereto an oligonucleotide comprising a first barcode selected from a pre-defined pool of first barcode, a second barcode selected from a pre-defined pool of second barcodes, and an adapter sequence; and attaching a nucleic acid sequence to the oligonucleotide via the adapter sequence.

According to still another set of embodiments, the method includes acts of encapsulating a plurality of cells and a plurality of particles within a plurality of microfluidic droplets, substantially each of the particles comprising an oligonucleotide and a nucleic acid sequence covalently bonded thereto, such that each droplet of the plurality of at least 10,000 droplets contains one or more oligonucleotides distinguishable from oligonucleotides contained in other droplets of the plurality of droplets; lysing at least some of the cells within the droplets to release nucleic acid from the cell, wherein the nucleic acid sequence comprises a portion able to interact with at least some of the released nucleic acid; and selectively amplifying portions of the released nucleic acid within the droplets to produce sequences comprising the amplifying portions and the oligonucleotide.

The method, in yet another set of embodiments, includes acts of providing a plurality of at least 10,000 microfluidic droplets containing cells, at least about 90% of the plurality of droplets containing one cell or no cell; lysing the cells within the plurality of microfluidic droplets to release nucleic acid from the cells; and producing selectively amplified nucleic acids within the droplets bound to oligonucleotides. In some cases, for at least about 90% of the droplets, the oligonucleotide within the droplet is distinguishable from oligonucleotides within other droplets of the plurality of droplets.

In another set of embodiments, the method includes providing a plurality of at least about 10,000 microfluidic droplets containing cells such that no more than 10% of the droplets contains two or more cells, lysing the cells within the plurality of droplets to release nucleic acid from the cells, and selectively amplifying portions of the released nucleic acid within the droplets to produce sequences comprising the amplifying portions and a droplet-specific barcode.

The method, in still another set of embodiments, includes acts of providing droplets containing cells such that no more than 10% of the droplets contains two or more cells, lysing the cells within the plurality of droplets to release nucleic acid from the cells, and selectively amplifying portions of the released nucleic acid within the droplets to produce sequences comprising the amplifying portions and a barcode selected from a pool of at least 10,000 distinguishable barcodes.

In another aspect, the present invention encompasses methods of making one or more of the embodiments described herein. In still another aspect, the present invention encompasses methods of using one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 1A-1B illustrate examples of the production of labeled nucleic acids, in one set of embodiments;

FIG. 3 illustrates yet another example of the production of labeled nucleic acids, in certain embodiments;

DETAILED DESCRIPTION

The present invention generally relates to microfluidics and labeled nucleic acids. For example, certain aspects are generally directed to systems and methods for labeling nucleic acids within microfluidic droplets or other compartments, for instance, arising from a cell. In one set of embodiments, particles may be prepared containing oligonucleotides that can be used to determine target nucleic acids, e.g., attached to the surface of the particles. The oligonucleotides may include "barcodes" or unique sequences that can be used to distinguish nucleic acids in a droplet from those in another droplet, for instance, even after the nucleic acids are pooled together or removed from the droplets. Certain embodiments of the invention are generally directed to systems and methods for attaching additional or arbitrary sequences to the nucleic acids within microfluidic droplets or other compartments, e.g., recognition sequences that can be used to selectively determine or amplify a desired sequence suspected of being present within a droplet. Such systems may be useful, for example, for selective amplification in various applications, such as high-throughput sequencing applications.

Some aspects of the present invention are generally directed to systems and methods for containing or encapsulating nucleic acids with oligonucleotides within microfluidic droplets or other suitable compartments, for example, microwells of a microwell plate, individual spots on a slide or other surface, or the like. The nucleic acids and the oligonucleotides may be ligated or attached together in some cases. The nucleic acids may arise from lysed cells or other material within the droplets. The oligonucleotides within a droplet may be distinguishable from oligonucleotides in other droplets, e.g., within a plurality or population of droplets. For instance, the oligonucleotides may contain one or more unique sequences or "barcodes" that are different between the various droplets. Thus, the nucleic acid within each droplet can be uniquely identified by determining the barcodes associated with the nucleic acid. This may be important, for example, if the droplets are "broken" or ruptured and the nucleic acids from different droplets are subsequently combined or pooled together, e.g., for sequencing or other analyses.

Figure 4:
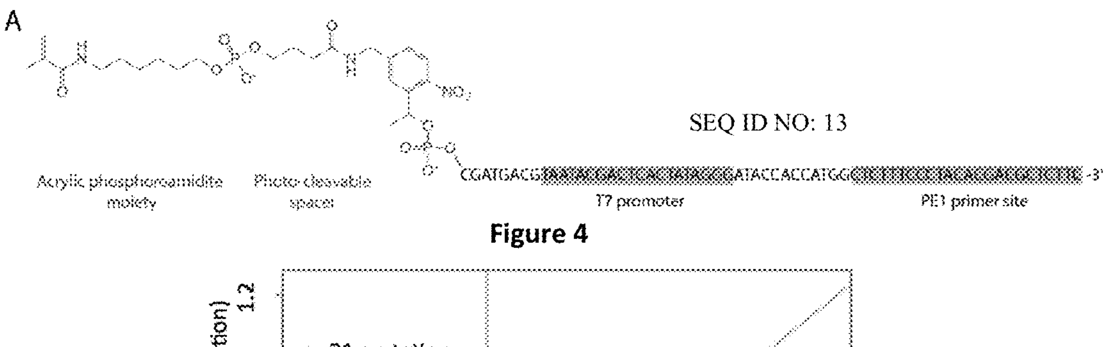
FIG. 4 illustrates a moiety containing a photocleavable spacer or linker, in some embodiments of the invention.

In some embodiments, the oligonucleotides are introduced into the droplets by initially attaching the oligonucleotides to a particle (e.g., a hydrogel or a polymeric particle), then subsequently releasing the oligonucleotides from the particle after the particle has been incorporated into a droplet. See, e.g., U.S. Pat. Apl. Ser. No. 62/072,944, filed Oct. 30, 2014 or PCT Apl. Ser. No. PCT/US2015/026443, filed on Apr. 17, 2015, entitled "Systems and Methods for Barcoding Nucleic Acids," each incorporated herein by reference. For example, in certain embodiments, the oligonucleotides may also contain a cleavable sequence or linker (e.g., as is shown in FIG. 4), or otherwise be releasable from the particles.

The particles may be prepared in some cases such that most or all of the particles have a uniquely distinguishable oligonucleotide, relative to other particles having other distinguishable oligonucleotides). If the particles are present within the droplets at a density of 1 particle/droplet (or less), then once the oligonucleotides are released from the particle, then most or all of the droplets will contain one unique oligonucleotide (or no unique oligonucleotide), thus allowing each droplet (and the nucleic acids contained therein) to be uniquely identified.

One example of an embodiment of the invention is now described with respect to FIG. 1. As will be discussed in more detail below, in other embodiments, other configurations may be used as well. FIG. 1A shows a particle (e.g., a hydrogel particle), one or more barcodes, and a "universal sequence" or an adapter sequence that can be used to attach or include any additional desired sequence to the oligonucleotides (e.g., a recognition sequence that can be used to recognize another entity, for example, a complementary sequence). These may be present or prepared in a bulk phase or within a droplet, such as a microfluidic droplet. In addition, other elements, such as promoters or enhancers may be present within the oligonucleotide as well, e.g., as shown in FIG. 1. In some embodiments, for example, the possible barcodes that are used within an oligonucleotide sequence are formed from two (or more) separate "pools" of barcode elements that are then joined together to produce the final barcode sequence, e.g., using a split-and-pool approach, as discussed below. In some cases, this may allow for very large numbers of possible barcodes to be used in an oligonucleotide, for instance, more than $10^4$ or $10^5$ potential barcodes.

The adaptor sequence may, in some embodiments, be exposed to a complementary sequence comprising a sequence that is complementary to the adapter. Other sequences, e.g., a primer, a promoter, etc. may also be present. Examples of primers, promoters, etc., are discussed herein. The complementary sequence may be able to bind to or otherwise associate with at least a portion of the adapter sequence, such as is shown in FIG. 1A. The complementary sequence may be fully complementary or contain one, two, three, or more mismatches, relative to the adapter sequence. The adapter sequence (and its complement) may be of any suitable length, e.g., 4, 5, 6, 7, 8, 9, 10, 11, 12, 13, 14, or 15 or more nucleotides.

For instance, is as shown in FIG. 1A, the complementary sequence may include a primer such as a gene-specific inner forward primer or a gene-specific reverse primer sequence, or other sequences as discussed herein. These may be useful, for example, to promote subsequent amplification or incorporation of a desired or arbitrary sequence into the oligonucleotide, e.g., attached to the particle. In FIG. 1A, this is the "template" strand. The primer may be one that is able to interact with the template, e.g., specifically (such as with a gene-specific inner forward primer) or nonspecifically. Subsequent amplification or incorporation, as is shown in FIG. 1A, may be used to incorporate the sequence of the template (or at least a portion thereof) into the oligonucleotide attached to the particle, thereby producing particles containing oligonucleotides containing one or more barcode sequences and a sequence corresponding to at least a portion of the template.

In some embodiments, the particles may be encapsulated in droplets, such as microfluidic droplets. Those of ordinary skill in the art will be aware of techniques for encapsulating particles within microfluidic droplets; see, for example, U.S. Pat. Nos. 7,708,949, 8,337,778, 8,765,485, or Int. Pat. Apl. Pub. Nos. WO 2004/091763 and WO 2006/096571, each incorporated herein by reference. In some cases, the particles may be encapsulated at a density of less than 1 particle/droplet (and in some cases, much less than 1 particle/droplet) to ensure that most or all of the droplets have only zero or one particle present in them.

The particles containing oligonucleotides (which may be attached to the surface of the particles, or otherwise contained or incorporated within the particles, etc.) may be used, in some embodiments, to determine or sequence nucleic acids arising from cells (or other samples), or for other applications. For instance, in the non-limiting example of FIG. 1B, a population of cells 10 is desired to be analyzed, e.g., by sequencing their DNA, by identifying certain proteins or genes that may be suspected of being present in at least some of the cells, by determining their mRNA or transcriptome, or the like. Although cells are used in this example as a source of nucleic acid material, this is by way of example, and in other embodiments, the nucleic acid may be introduced into the droplets from other sources, or using other techniques.

The cells may first be encapsulated within the microfluidic droplets 40, e.g., using techniques known to those of ordinary skill in the art. In some cases, the cells may be encapsulated at a density of less than 1 cell/droplet (and in some cases, much less than 1 cell/droplet) to ensure that most or all of the droplets have only zero or one cell present in them. Thus, as is shown in FIG. 1B, each of droplets 41, 42, 43 . . . have either zero or one cell present in them.

Also encapsulated in the droplets are oligonucleotide 20, present on particles 30. As noted above, particles 30 may be, for example, microparticles, and may be a hydrogel or a polymeric particle, or other types of particles such as those described herein. The particles and the cells may be encapsulated within the droplets simultaneously or sequentially, in any suitable order. In one set of embodiments, each particle contains a unique oligonucleotide, although there may be multiple copies of the oligonucleotide present on a particle. For instance, each of the oligonucleotides may have one or more barcodes. Thus, for example, particle 31 contains only copies of oligonucleotide 21, particle 32 contains only copies of oligonucleotide 22, particle 33 contains only copies of oligonucleotide 33, etc.

Figure 1B:
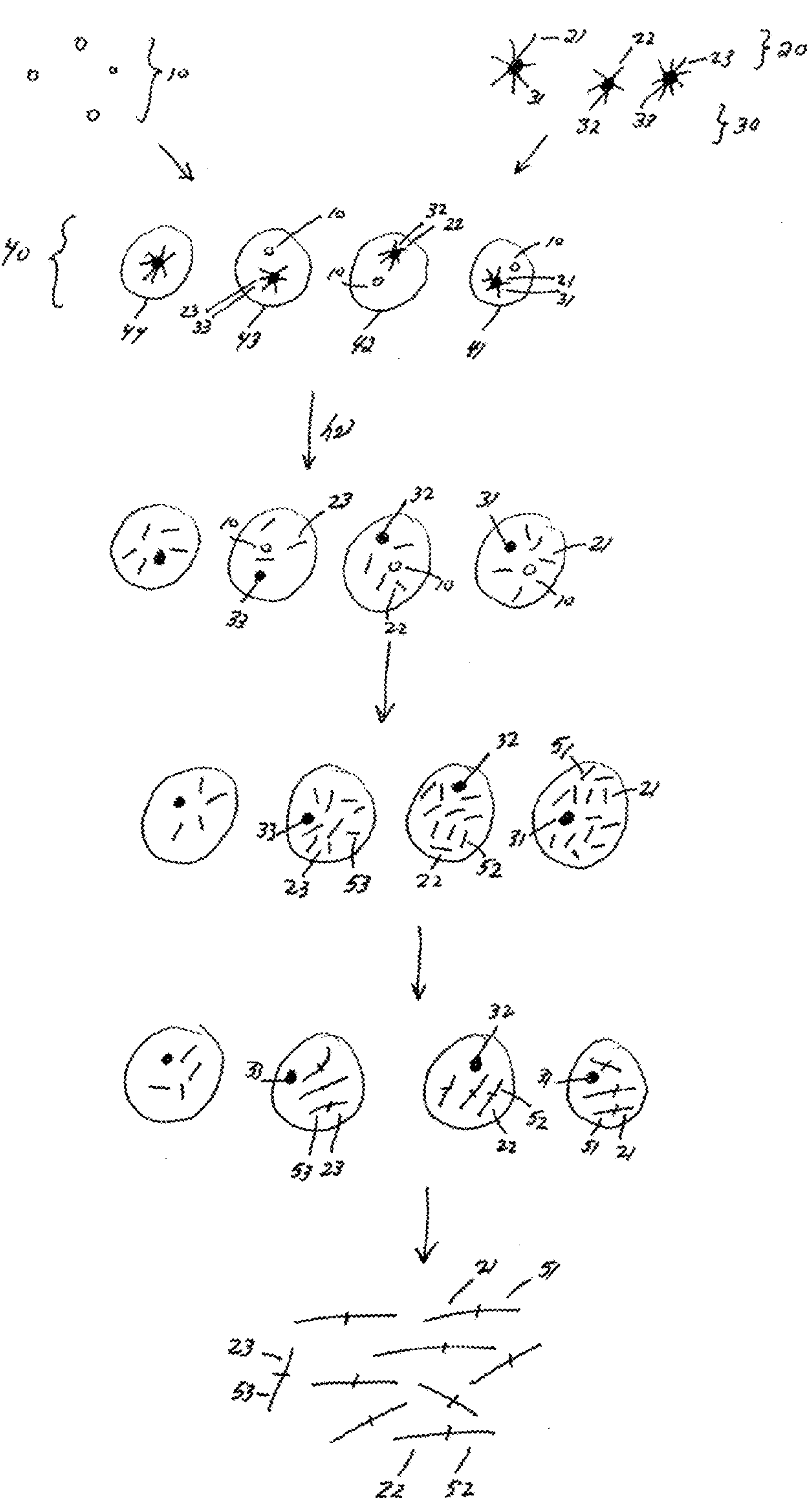

It should be noted that according to certain embodiments of the invention, the oligonucleotide are initially attached to particles to facilitate the introduction of only one unique oligonucleotide to each droplet, as is shown in FIG. 1B. (In other embodiments, however, a plurality of oligonucleotides and/or particles may be present in a droplet, e.g., containing the same unique barcode.) For example, if the particles are present in the droplets at a density of less than 1 particle/droplet, then most or all of the droplets will each have only a single particle, and thus only a single type of oligonucleotide, that is present. Accordingly, as is shown in FIG. 1B, the oligonucleotide may be cleaved or otherwise released from the particles, e.g., such that each droplet 41, 42, 43, . . . contains a unique oligonucleotide 21, 22, 23, . . . that is different than the other oligonucleotide that may be present in the other droplets. Thus, each oligonucleotide present within a droplet will be distinguishable from the oligonucleotides that are present in the other droplets. Although light (hv) is used in FIG. 1B to cleave the oligonucleotides from the particles, it should be understood that this is by way of example only, and that other methods of cleavage or release can also be used, e.g., as discussed herein. For example, in one set of embodiments, agarose particles containing oligonucleotides (e.g., physically) may be used, and the oligonucleotides may be released by heating the agarose, e.g., until the agarose at least partially liquefies or softens.

In some cases, the cells are lysed to release nucleic acid or other materials 51, 52, 53, . . . from the cells. For example, the cells may be lysed using chemicals or ultrasound. The cells may release, for instance, DNA, RNA, mRNA, proteins, enzymes or the like. In some cases, the nucleic acids that are released may optionally undergo amplification, for example, by including suitable reagents specific to the amplification method. Examples of amplification methods known to those of ordinary skill in the art include, but are not limited to, polymerase chain reaction (PCR), reverse transcriptase (RT) PCR amplification, in vitro transcription amplification (IVT), multiple displacement amplification (MDA), or quantitative real-time PCR (qPCR).

Some or all of the nucleic acid or other material 51, 52, 53, . . . may be associated with the oligonucleotides present in the droplets, e.g., by covalently bonding. For example, the nucleic acid or other material 51, 52, 53 may be ligated or enzymatically attached to the oligonucleotides present in the droplets. Thus, as is shown in FIG. 1B, droplet 41 exhibits nucleic acids 51 attached to oligonucleotides 21, droplet 42 exhibits nucleic acids 52 attached to oligonucleotides 22, droplet 43 exhibits nucleic acids 53 attached to oligonucleotides 23, etc. Thus, the nucleic acids within each droplet are distinguishable from the nucleic acids within the other droplets of the plurality of droplets 50 by way of the oligonucleotides, which are unique to each droplet in this example.

It should also be understood that although FIG. 1B depicts cleavage of the oligonucleotides from the particles followed by lysis of the cells, in other embodiments, these need not necessarily occur in this order. For example, cell lysis may occur after cleavage, or both may occur simultaneously.

Droplet 41, 42, 43, . . . may then in some cases be "burst" or "broken" to release their contents, and in some cases, the nucleic acids present in each droplet may be combined or pooled together, as is shown in FIG. 1B. However, since the nucleic acids are labeled by the different oligonucleotides, the nucleic acids from one droplet (i.e., from one cell) can still be distinguished from those from other droplets (or other cells) using the oligonucleotides (e.g., by determining barcodes on the oligonucleotides). Accordingly, subsequent analysis (e.g., sequencing) of the combined pool of nucleic acids may be performed, and the source of each nucleic acid (e.g., individual cells) may be determined be determining the different oligonucleotides.

Thus, for example, a population of normal cells and cancer cells (e.g., arising from a tissue sample or biopsy) may be analyzed in such a fashion, and the cancer cells may be identified as having abnormal DNA, even if present in a large pool of normal cells. For example, due to the ability to track DNA on a cellular level using the oligonucleotides, the abnormal DNA can still be identified even if outnumbered by a large volume of normal DNA. As other non-limiting examples, stem cells may be isolated from normal cells, or the isolation of rare cell types in a population of interest may be performed.

Figure 2:
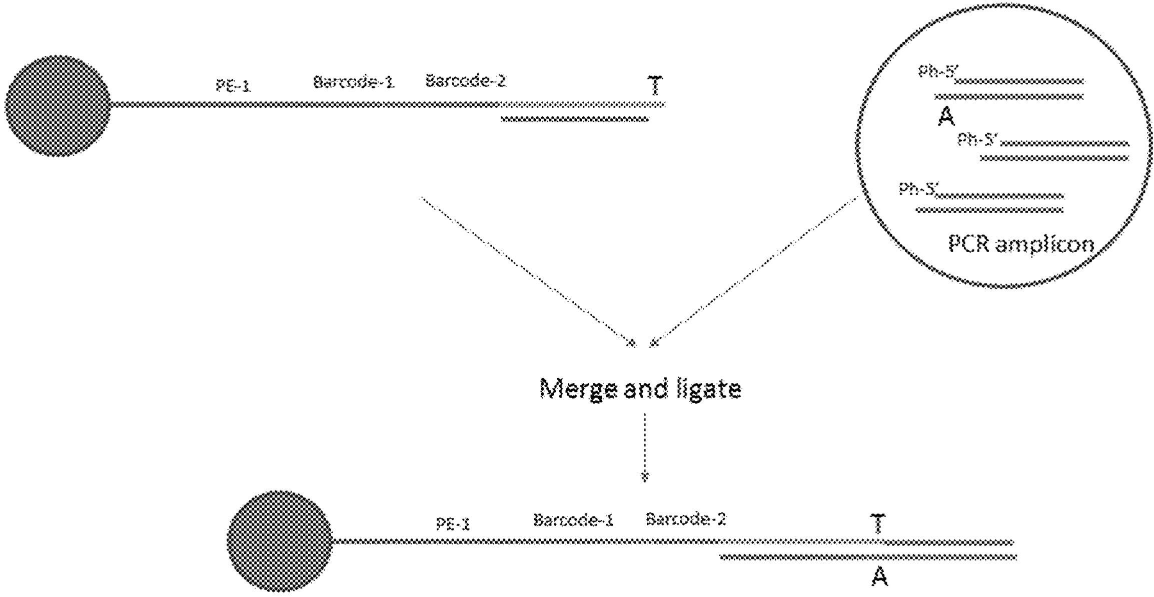
FIG. 2 illustrates another example of the production of labeled nucleic acids, in certain embodiments.

FIG. 2 illustrates another example method of producing particles containing oligonucleotides, e.g., attached to the surface or otherwise incorporated within the particle. Similar to FIG. 1A, FIG. 2 shows a particle having attached thereto one or more barcodes. Optionally, the oligonucleotide may also contain a cleavable linker, such as photocleavable linker. Other sequences may also be present as well, e.g., primers such as PE1. In FIG. 2, an overhang region (e.g., comprising thymine in this example) may be matched to sequences that contain a complementary overhanging region (e.g., comprising adenine). The overhanging region may contain any suitable number of nucleotides, e.g., 1, 2, 3, 4, 5, etc.

A suitable sequence may be separately amplified, e.g., within a droplet or in bulk solution, to produce a plurality of "amplicon" sequences that can then be attached to the oligonculeotides, e.g., using the overhang region. Such a system may be useful, for example, so that the amplicon sequences are attached primarily to the oligonucleotide (due to the presence of the overhang region) and not to each other or to oligonculeotides that already contain an amplicon sequence (i.e., since the overhang region is already occupied by the amplicon sequence). The suitable sequence may be, for example, single-stranded or double-stranded, and may be amplified using PCR or any other suitable technique, including those described herein. For instance, in some cases, the sequences may be amplified using various techniques, e.g., amplified within a microfluidic droplet as is shown in FIG. 2. See, for example, U.S. Pat. Apl. Ser. Nos. 61/981,108, 62/072,944, or 62/133,140, each incorporated by reference in its entirety.

In such a manner, a particle may be prepared containing one or more oligonucleotides (for example, containing labels such as barcode, promoters, primers, or the like), and the oligonucleotides may be attached to a desired a desired or arbitrary sequence (e.g., arising from a template), e.g., for subsequent use. As with FIG. 1A, this may be used to particles containing oligonucleotides containing one or more barcode sequences and a sequence corresponding to at least a portion of a template.

In some embodiments, as is shown in the example of FIG. 2, the particles may be contained within a first plurality of droplets (e.g., at a density of less than 1 particle/droplet to ensure that most or all of the droplets have only zero or one particle present in them, although this is not a requirement in all embodiments), and the amplicons may be contained within a second plurality of droplets. If droplets are used, the droplets may be merged together, e.g., using known techniques (see, for instance U.S. Pat. Apl. Pub. Nos. 2006/0163385, 2007/0003442, or 2010/0172803, each incorporated herein by reference). Similarly, bulk solutions (containing amplicons) may be directly injected into droplets, for instance, using known techniques such as picoinjection or other methods discussed in Int. Pat. Apl. Pub. No. WO 2010/151776, entitled "Fluid Injection" (incorporated herein by reference)

After being brought together, the nucleic acids may be bonded to the oligonucleotides, e.g., covalently, through primer extension, through ligation, or the like. Any of a wide variety of different techniques may be used, and those of ordinary skill in the art will be aware of many such techniques. The exact joining technique used is not necessarily critical, and can vary between embodiments. Non-limiting examples include ligases or other suitable techniques such as those discussed in U.S. Pat. Apl. Ser. No. 61/981,123, incorporated herein by reference.

FIG. 3 illustrates yet another system for producing particles containing oligonucleotides, similar to FIG. 2. As above, a suitable sequence may be separately amplified, e.g., using PCR or other suitable techniques, to produce a plurality of "amplicon" sequences that can then be attached to the oligonculeotides. In this example, overhang regions may be prepared using restriction enzymes that may be used to cut or cleave the ends of the nucleic acids and the oligonucleotides to produce complementary overhang regions that may be joined together to produce the final oligonucleotide. Each of the nucleic acids and the oligonucleotides may thus be designed to contain a suitable restriction site that may be recognized and cleaved by a restriction endonuclease. Non-limiting examples of restriction endonucleases include EcoRI, EcoRII, BamHI, HindIII, TaqI, EcoP15, and SmaI. Many restriction endonucleases are commercially available. In addition, in some embodiments, enzymes that can cleave and ligate fragments together may be used, for example, GENEART® Type IIs (LifeTechnologies).

Thus, certain aspects of the invention are generally directed to systems and methods for attaching nucleic acids to oligonucleotides attached to or otherwise associated with particles. The nucleic acid may be any suitable nucleic acid sequence, and in some cases may be arbitrary. For instance, in some embodiments, particles containing oligonucleotides may be prepared and sent to a user, who then adds a desired nucleic acid to the oligonucleotides attached to the particles, e.g., using techniques such as those described herein.

In one set of embodiments, for example, the nucleic acid to be attached to the oligonucleotides may include a target sequence or template, and/or include a recognition sequence that is able to recognize a desired nucleic acid sequence. In certain cases, the recognition sequence may be able to recognize genomic DNA such as human genomic DNA, or a specific portion, such as a gene. The recognition sequence may also be able to associate with an RNA sequence (e.g., an mRNA sequence). The recognition sequence may be complementary to a target sequence, or contain a number of mismatches, e.g., 1, 2, 3, or 4 or more mismatches. In some cases, the recognition sequence may be at least about 80%, at least about 85%, at least about 90%, at least about 95%, or at least about 97% complementary to a target sequence.

The nucleic acid may also include, in some embodiments, other sequences, such as a primer, a promoter, etc. For example, a primer may be present to allow for amplification, sequencing, etc. of the nucleic acid, e.g., as discussed herein. Non-limiting examples include a gene-specific inner forward primer or a gene-specific reverse primer sequence, or other sequences as discussed herein.

As mentioned, in some embodiments, the nucleic acid may be amplified prior to association with the oligonucleotides. Any suitable amplification technique may be used, for instance, PCR, assembly PCR, polymerase cycling assembly, reverse transcriptase (RT) PCR amplification, in vitro transcription amplification (IVT), multiple displacement amplification (MDA), or quantitative real-time PCR (qPCR), or the like. The target sequence or template may be amplified within droplets (see, e.g., U.S. Pat. Apl. Pub. No. 2010/0136544, 2014/0199730, or 2014/0199731), or in bulk solution.

In one set of embodiments, the nucleic acid may be attached to an oligonucleotide. As discussed below, the oligonucleotide may be attached to or otherwise incorporated or contained within a particle. In one set of embodiments, the nucleic acid may be added to the oligonucleotide using a ligase or other suitable enzyme that can directly attach the nucleic acid to the oligonucleotides, e.g., to a free end of the oligonucleotide. See, e.g., U.S. Pat. Apl. Ser. No. 62/072,944, filed Oct. 30, 2014 or PCT Pat. Apl. Ser. No. PCT/US2015/026443, filed on Apr. 17, 2015, entitled “Systems and Methods for Barcoding Nucleic Acids,” each incorporated herein by reference.

Non-limiting examples of ligases include DNA ligases such as DNA Ligase I, DNA Ligase II, DNA Ligase III, DNA Ligase IV, T4 DNA ligase, T7 DNA ligase, T3 DNA Ligase, *E. coli* DNA Ligase, Taq DNA Ligase, or the like. Many such ligases may be purchased commercially. In addition, in some embodiments, two or more nucleic acids may be ligated together using annealing or a primer extension method. In addition, in some cases, the nucleic acid may be added internally of an oligonucleotide, e.g., using transposons or the like. See, e.g., U.S. Pat. Apl. Ser. No. 62/072,950, incorporated herein by reference in its entirety.

In some embodiments, the nucleic acid and the oligonucleotide may have straight or “sticky” ends, e.g., containing overhangs of unpaired nucleotides that may be complementary. Non-limiting examples include those described in FIGS. 2 and 3. In some cases, e.g., as shown in FIG. 3, restriction enzymes may be used to prepare the ends of the nucleic acids prior to joining.

Thus, for example, the nucleic acid may contain a portion of unpaired nucleotides, and the oligonucleotide may contain a complementary portion of unpaired nucleotides. As a non-limiting example, the overhang may be an A and the complement may be a T. The overhanging region may contain any suitable number of nucleotides, e.g., 1, 2, 3, 4, 5, 6, 7, 8, 9, 10, etc. The overhang region may contain only a single nucleotide (e.g., A, AA, AAA, etc.) or a random or any other sequence of suitable nucleotides. In some cases, the overhang may be created using a suitable enzyme, e.g., a restriction endonuclease or a reverse transcriptase.

For instance, in one non-limiting embodiment, the 3' end of a barcoded primer is terminated with a poly-T sequences that may be used to capture cellular mRNA for whole-transcriptome profiling. The resulting library combining all cells can optionally be enriched using PCR-based methods or using hybridization capture-based methods (such as Agilent SureSelect), e.g., to allow sequencing of only a sub-set of genes of interest. In another embodiment, the 3' end of the barcoded primers may terminate with a random DNA sequence that can be used to capture the RNA in the cell. In another embodiment, the 3' end of the barcoded primers may terminate with a specific DNA sequence, e.g., that can be used to capture DNA or RNA species (“genes”) of interest, or to hybridize to a DNA probe that is delivered into the droplets in addition to the particles or microspheres, for example, together with the enzyme reagents. In another embodiment, a particle or microsphere may carry a number of different primers to target several genes of interest. Yet another embodiment is directed to optimization of the size of droplets and the concentration of reaction components required for droplet barcoding.

In another set of embodiments, a nucleic acid may be attached to an oligonucleotide using a sequence that is complementary to an adapter sequence on the oligonucleotide, where the complementary sequence contains a primer that can be used to amplify or incorporate a desired or arbitrary sequence (e.g., a template) to the oligonucleotide, e.g., as discussed in FIG. 1A.

For instance, in some embodiments, a template may be introduced into a droplet and amplified within the droplet. If the droplet contains oligonucleotides, then the amplification process may also be used to attach the template to the oligonucleotide, e.g., via a complementary sequence containing primers able to recognize at least a portion of the template. For example, the oligonucleotide may contain a “universal” or adapter sequence, which is complementary to a complementary sequence containing a portion complementary to the adapter sequence and a primer able to recognize at least a portion of the template. Upon amplification within the droplet, the oligonucleotide may thus be extended, e.g., to contain the template. Thus, upon amplification, the template sequence may become incorporated into the oligonucleotide, e.g., as is shown in FIG. 1, and the primer may be used to facilitate amplification or joining of a template strand or other sequences to the oligonucleotide. For example, this process may be facilitated using primers such as gene-specific primers (forward or reverse) within the complementary sequence.

The oligonucleotide to which the nucleic acid is attached to may contain, for example, barcode sequences, recognition sequences, cleavable linkages, random sequences, or other sequences such as any of those discussed herein. For example, in one set of embodiments, the nucleic acids may be attached to specific oligonucleotides (e.g., barcodes”) that can be used to distinguish nucleic acids from one source (e.g., from a cell contained within a droplet) from those from other sources (e.g., from other cells). One or more than one barcode may be present on an oligonucleotide.

In some embodiments, the oligonucleotides may comprise a “barcode” or a unique sequence. The sequence may be selected such that some or most of the oligonucleotides (e.g., present on a particle and/or in a droplet) have the unique sequence (or combination of sequences that is unique), but other oligonucleotides (e.g., on other particles or droplets)

do not have the unique sequence or combination of sequences. Thus, for example, the sequences may be used to uniquely identify or distinguish a droplet, or nucleic acid contained arising from the droplet (e.g., from a lysed cell) from other droplets, or other nucleic acids (e.g., released from other cells) arising from other droplets.

The sequences may be of any suitable length. The length of the barcode sequence is not critical, and may be of any length sufficient to distinguish the barcode sequence from other barcode sequences. One, two, or more "barcode" sequence may be present in an oligonucleotide, as discussed above. A barcode sequence may have a length of 5, 6, 7, 8, 9, 10, 11, 12, 13, 14, 15, 16, 17, 18, 19, 20, 21, 22, 23, 24, or 25 nt. More than 25 nucleotides may also be present in some cases.

In some cases, the unique or barcode sequences may be taken from a "pool" of potential barcode sequences. If more than one barcode sequence is present in an oligonucleotide, the barcode sequences may be taken from the same, or different pools of potential barcode sequences. The pool of sequences may be selected using any suitable technique, e.g., randomly, or such that the sequences allow for error detection and/or correction, for example, by being separated by a certain distance (e.g., Hamming distance) such that errors in reading of the barcode sequence can be detected, and in some cases, corrected. The pool may have any number of potential barcode sequences, e.g., at least 100, at least 300, at least 500, at least 1,000, at least 3,000, at least 5,000, at least 10,000, at least 30,000, at least 50,000, at least 100,000, at least 300,000, at least 500,000, or at least 1,000,000 barcode sequences.

Thus, some embodiments of the present invention are generally directed to barcoded nucleic acids attached to particles or microspheres. For example, one set of embodiments is generally directed to particles or microspheres carrying nucleic acid fragments (each encoding a barcode, a primer, and/or other sequences possibly used for capture, amplification and/or sequencing of nucleic acids). Microspheres may refer to a hydrogel particle (polyacrylamide, agarose, etc.), or a colloidal particle (polystyrene, magnetic or polymer particle, etc.) of 1 to 500 micrometer in size, or other dimensions such as those described herein. The microspheres may be porous in some embodiments. Other suitable particles or microspheres that can be used are discussed in more detail herein.

The preparation of particles or microspheres, in some cases, may rely on the covalent attachment or other techniques of incorporation of an initial DNA oligonucleotide to the particles or microspheres, followed by enzymatic extension of each oligonucleotide by one or more barcodes selected, e.g., at random, from a pre-defined pool. The final number of possible unique barcodes may depend in some cases on the size of the pre-defined barcode pool and/or on the number of extension steps. For example, using a pool of 384 pre-defined barcodes and 2 extension steps, each particle or microsphere carries one of 3842=147,456 possible barcodes; using 3 extension steps, each particle or microsphere carries one of 3843=56,623,104 possible barcodes; and so on. Other numbers of steps may also be used in some cases; in addition, each pool may have various numbers of pre-defined barcodes (not just 384), and the pools may have the same or different numbers of pre-defined barcodes. The pools may include the same and/or different sequences.

Accordingly, in some embodiments, the possible barcodes that are used are formed from one or more separate "pools" of barcode elements that are then joined together to produce the final barcode, e.g., using a split-and-pool approach. A pool may contain, for example, at least about 300, at least about 500, at least about 1,000, at least about 3,000, at least about 5,000, or at least about 10,000 distinguishable barcodes. For example, a first pool may contain $x_1$ elements and a second pool may contain $x_2$ elements; forming a barcode containing an element from the first pool and an element from the second pool may yield, e.g., $x_1x_2$ possible barcodes that could be used. It should be noted that $x_1$ and $x_2$ may or may not be equal. This process can be repeated any number of times; for example, the barcode may include elements from a first pool, a second pool, and a third pool (e.g., producing $x_1x_2x_3$ possible barcodes), or from a first pool, a second pool, a third pool, and a fourth pool (e.g., producing $x_1x_2x_3x_4$ possible barcodes), etc. There may also be 5, 6, 7, 8, or any other suitable number of pools. Accordingly, due to the potential number of combinations, even a relatively small number of barcode elements can be used to produce a much larger number of distinguishable barcodes.

In some cases, such use of multiple pools, in combination, may be used to create substantially large numbers of useable barcodes, without having to separately prepare and synthesize large numbers of barcodes individually. For example, in many prior art systems, requiring 100 or 1,000 barcodes would require the individual synthesis of 100 or 1,000 barcodes. However, if larger numbers of barcodes are needed, e.g., for larger numbers of cells to be studied, then correspondingly larger numbers of barcodes would need to be synthesized. Such systems become impractical and unworkable at larger numbers, such as 10,000, 100,000, or 1,000,000 barcodes. However, by using separate "pools" of barcodes, larger numbers of barcodes can be achieved without necessarily requiring each barcode to be individually synthesized. As a non-limiting example, a first pool of 1,000 distinguishable barcodes (or any other suitable number) and a second pool of 1,000 distinguishable barcodes can be synthesized, requiring the synthesis of 2,000 barcodes (or only 1,000 if the barcodes are re-used in each pool), yet they may be combined to produce 1,000×1,000=1,000,000 distinguishable barcodes, e.g., where each distinguishable barcode comprises a first barcode taken from the first pool and a second barcode taken from the second pool. Using 3, 4, or more pools to assemble the barcode may result in even larger numbers of barcodes that may be prepared, without substantially increasing the total number of distinguishable barcodes that would need to be synthesized.

The oligonucleotide may be of any suitable length or comprise any suitable number of nucleotides. The oligonucleotide may comprise DNA, RNA, and/or other nucleic acids such as PNA, and/or combinations of these and/or other nucleic acids. In some cases, the oligonucleotide is single stranded, although it may be double stranded in other cases. For example, the oligonucleotide may have a length of at least about 10 nt, at least about 30 nt, at least about 50 nt, at least about 100 nt, at least about 300 nt, at least about 500 nt, at least about 1000 nt, at least about 3000 nt, at least about 5000 nt, at least about 10,000 nt, etc. In some cases, the oligonucleotide may have a length of no more than about 10,000 nt, no more than about 5000 nt, no more than about 3000 nt, no more than about 1000 nt, no more than about 500 nt, no more than about 300 nt, no more than about 100 nt, no more than about 50 nt, etc. Combinations of any of these are also possible, e.g., the oligonucleotide may be between about 10 nt and about 100 nt. The length of the oligonucleotide is not critical, and a variety of lengths may be used in various embodiments.

The oligonucleotide may also contain a variety of sequences. For example, the oligonucleotide may contain one or more primer sequences, one or more unique or "barcode" sequences as discussed herein, one or more promoter sequences, one or more spacer sequences, or the like. The oligonucleotide may also contain, in some embodiments one or more cleavable spacers, e.g., photocleavable linker. The oligonucleotide may in some embodiments be attached to a particle chemically (e.g., via a linker) or physically (e.g., without necessarily requiring a linker), e.g., such that the oligonucleotides can be removed from the particle via cleavage. Other examples include portions that may be used to increase the bulk (or length) of the oligonucleotides (e.g., using specific sequences or nonsense sequences), to facilitate handling (for example, an oligonucleotide may include a poly-A tail), to increase selectivity of binding (e.g., as discussed below), to facilitate recognition by an enzyme (e.g., a suitable ligase), to facilitate identification, or the like. Examples of these and/or other sequences are described in further detail herein.

In some cases, the oligonucleotide may contain one or more promoter sequences, e.g., to allow for production of the oligonucleotide, to allow for enzymatic amplification, or the like. Those of ordinary skill in the art will be aware of primer sequences, e.g., P5 or P7. Many such primer sequences are available commercially. Examples of promoters include, but are not limited to, T7 promoters, T3 promoters, or SP6 promoters.

In some cases, the oligonucleotide may contain one or more primer sequences. Typically, a primer is a single-stranded or partially double-stranded nucleic acid (e.g., DNA) that serves as a starting point for nucleic acid synthesis, allowing polymerase enzymes such as nucleic acid polymerase to extend the primer and replicate the complementary strand. A primer may be complementary to and to hybridize to a target nucleic acid. In some embodiments, a primer is a synthetic primer. In some embodiments, a primer is a non-naturally-occurring primer. A primer typically has a length of 10 to 50 nucleotides. For example, a primer may have a length of 10 to 40, 10 to 30, 10 to 20, 25 to 50, 15 to 40, 15 to 30, 20 to 50, 20 to 40, or 20 to 30 nucleotides. In some embodiments, a primer has a length of 18 to 24 nucleotides. Examples of primers include, but are not limited to, P5 primer, P7 primer, PE1 primer, PE2 primer, A19 primer, or other primers discussed herein.

In some cases, the oligonucleotide may contain nonsense or random sequences, e.g., to increase the mass or size of the oligonucleotide. The random sequence can be of any suitable length, and there may be one or more than one present. As non-limiting examples, the random sequence may have a length of 10 to 40, 10 to 30, 10 to 20, 25 to 50, 15 to 40, 15 to 30, 20 to 50, 20 to 40, or 20 to 30 nucleotides.

In some cases, the oligonucleotide may comprise one or more sequences able to specifically bind a gene or other entity. For example, in one set of embodiments, the oligonucleotide may comprise a sequence able to recognize mRNA, e.g., one containing a poly-T sequence (e.g., having several T's in a row, e.g., 4, 5, 6, 7, 8, or more T's).

In one set of embodiments, the oligonucleotide may contain one or more cleavable linkers, e.g., that can be cleaved upon application of a suitable stimulus. For example, the cleavable sequence may be a photocleavable linker that can be cleaved by applying light or a suitable chemical or enzyme. A non-limiting example of a photocleavable linker can be seen in FIG. 4. In some cases, for example, a plurality of particles (containing oligonucleotides on their surfaces) may be prepared and added to droplets, e.g., such that, on average, each droplet contains one particle, or less (or more) in some cases. After being added to the droplet, the oligonucleotides may be cleaved from the particles, e.g., using light or other suitable cleavage techniques, to allow the oligonucleotides to become present in solution, i.e., within the interior of the droplet. In such fashion, oligonucleotides can be easily loaded into droplets by loading of the particles into the droplets, then cleaved off to allow the oligonucleotides to be in solution, e.g., to interact with nucleotides or other species, such as is discussed herein.

A variety of techniques may be used for preparing oligonucleotides such as those discussed herein. These may be prepared in bulk and/or in one or more droplets, such as microfluidic droplets. In some cases, the oligonucleotides may be prepared in droplets, e.g., to ensure that the barcodes and/or oligonucleotides within each droplet are unique. In addition, in some embodiments, particles may be prepared containing oligonucleotides with various barcodes in separate droplets, and the particles may then be given or sold to a user who then adds the nucleic acids to the oligonucleotides, e.g., as described above.

In some cases, an oligonucleotide comprising DNA and/or other nucleic acids may be attached to particles and delivered to the droplets. In some cases, the oligonucleotides are attached to particles to control their delivery into droplets, e.g., such that a droplet will typically have at most one particle in it. In some cases, upon delivery into a droplet, the oligonucleotide may be removed from the particle, e.g., by cleavage, by degrading the particle, etc. However, it should be understood that in other embodiments, a droplet may contain 2, 3, or any other number of particles, which may have oligonucleotides that are the same or different.

In another aspect, the present invention provides systems and methods for determining or identifying DNA or RNA from large numbers of cells, e.g., genomic DNA, specific genes, specific mRNA sequences, or the like. In some embodiments, the present invention provides systems and methods for the parallel capture and barcoding of DNA or RNA from large numbers of cells, e.g., for the purpose of profiling cell populations, or other purposes such as those described herein. In some embodiments, this relies on the encapsulation of barcoded nucleic acids or other suitable oligonucleotides, e.g., attached to particles or microspheres (for example, hydrogel or polymer microspheres) together with cells and/or other reagents that may be used for RNA and/or DNA capture and/or amplification.

In one set of embodiments, the contents arising from substantially each individual cell may be labeled, e.g., with a unique barcode (which may be randomly determined, or determined as discussed herein), which may allow in some cases for hundreds, thousands, tens of thousands, or even hundreds of thousands or more of different cells to be barcoded or otherwise labeled in a single experiment, e.g., to determine or define the heterogeneity between cells in a population or for screening cell populations, etc. Other purposes have been described herein.

In one set of embodiments, a microfluidic system is used to capture single cells into individual droplets (e.g., 50 pL to 10 nL volume), e.g., in a single reaction vessel. Each cell may be lysed and its RNA and/or DNA uniquely barcoded or labeled with a droplet-specific barcode, e.g., through an enzymatic reaction, through ligation, etc. Examples of microfluidic systems, including those with dimensions other than these, are also provided herein. Some embodiments might also be used, in some embodiments, to quantify protein abundance in single cells in parallel to RNA or DNA, e.g., by first treating cells with DNA-tagged antibodies, in which case the DNA tags can be similarly barcoded with a droplet-specific barcode. Once the cell components in droplets have been barcoded, the droplets may be broken or burst and the sample can be processed, e.g., in bulk, for high-throughput sequencing or other applications. After sequencing, the data can be split or otherwise analyzed according to the DNA barcodes.

To perform parallel barcoding of DNA, RNA and/or DNA-antibody tags in single cells, a single hydrogel or polymer particle or microsphere may be encapsulated into each droplet together with biological or chemical reagents and a cell, in accordance with one set of embodiments. Particles or microspheres carrying a high concentration (e.g. 1 to 100 micromolar) of DNA fragments (hereafter "primers") may encode (a) a barcode sequence selected at random from a pool of, e.g., at least 10,000 barcodes (or at least 30,000 barcodes, at least 100,000 barcodes, at least 300,000 barcodes, or at least 1,000,000 barcodes, etc.), with the same barcode found on all nucleic acid fragments on the particles or microspheres; and/or encode (b) one or more a primer sequences used for hybridization and capture of DNA or RNA. The number of distinct barcodes may be at least 10-fold, and in some cases at least 100-fold, larger than the number of cells to be captured, in order to reduce the possibility of two or more cells occupying different droplets with particles or microspheres that carry the same barcode. For example, with 150,000 barcodes and 1,000 cells, on average just 3 cells will acquire a duplicate barcode (resulting in 997 detected barcodes).

In some embodiments, the encapsulation conditions are chosen such droplets contain one particle (or microsphere) and one cell. The presence of empty droplets and/or droplets with single particles but without cells, and/or droplets with cells but without particles, may not substantially affect performance. However, the presence of two or more particles or two or more cells in one droplet may lead to errors that can be difficult to control for, so the incidence of such events is kept to minimum in some instances, for example, less than about 10% or less than about 5%. Excepting the cells and particles, other biological and chemical reagents may be distributed equally among the droplets. The co-encapsulated cells and particles may be collected and processed according to the aim of the particular application. For example, in one particular embodiment, the DNA or RNA of single cells is captured by the primers introduced with particle, and may then be converted into barcoded complimentary DNA upon reverse transcription or other DNA polymerization reaction.

After purification and optional DNA amplification, the base composition and barcode identity of cellular nucleic acids may be determined, for instance, by sequencing or other techniques. Alternatively, in some embodiments, primers introduced with particles or microspheres can be used for amplification of specific nucleic acid sequences from a genome.

In some embodiments, the barcoded primers introduced using particles or microspheres can be cleaved therefrom by, e.g., light, chemical, enzymatic or other techniques, e.g., to improve the efficiency of priming enzymatic reactions in droplets. However, the cleavage of the primers can be performed at any step or point, and can be defined by the user in some cases. Such cleavage may be particularly important in certain circumstances and/or conditions; for example, some fraction of RNA and DNA molecules in single cells might be very large, or might be associated in complexes and therefore will not diffuse efficiently to the surface or interior of the particle or microsphere. However, in other embodiments, cleavage is not essential.

Techniques such as these can be used to analyze, for example, genomes, single nucleotide polymorphisms, specific gene expression levels, non-coding RNA, the whole transcriptome (or a portion thereof), entire genes or their sections, etc. However, the invention should not be limited to only these applications.

In one non-limiting embodiment, the 3' end of a barcoded primer is terminated with a poly-T sequences that may be used to capture cellular mRNA for whole-transcriptome profiling. The resulting library combining all cells can optionally be enriched using PCR-based methods or using hybridization capture-based methods (such as Agilent SureSelect), e.g., to allow sequencing of only a sub-set of genes of interest. In another embodiment, the 3' end of the barcoded primers may terminate with a random DNA sequence that can be used to capture the RNA in the cell. In another embodiment, the 3' end of the barcoded primers may terminate with a specific DNA sequence, e.g., that can be used to capture DNA or RNA species ("genes") of interest, or to hybridize to a DNA probe that is delivered into the droplets in addition to the particles or microspheres, for example, together with the enzyme reagents. In another embodiment, a particle or microsphere may carry a number of different primers to target several genes of interest. Yet another embodiment is directed to optimization of the size of droplets and the concentration of reaction components required for droplet barcoding.

The oligonucleotide may be attached to a particle, e.g., as discussed herein. In some embodiments, a particle may comprise only one oligonucleotide, although multiple copies of the oligonucleotide may be present on the particle; other particles may comprise different oligonucleotides that are distinguishable, e.g., using the barcode sequences described herein.

Any suitable method may be used to attach the oligonucleotide to the particle. The exact method of attachment is not critical, and may be, for instance, chemical or physical. For example, the oligonucleotide may be covalently bonded to the particle via a biotin-steptavidin linkage, an amino linkage, or an acrylic phosphoramidite linkage. See, e.g., FIG. 20A for an example of an acrylic phosphoramidite linkage. In another set of embodiments, the oligonucleotide may be incorporated into the particle, e.g., physically, where the oligonucleotide may be released by altering the particle. Thus, in some cases, the oligonucleotide need not have a cleavable linkage. For instance, in one set of embodiments, an oligonucleotide may be incorporated into particle, such as an agarose particle, upon formation of the particle. Upon degradation of the particle (for example, by heating the particle until it begins to soften, degrade, or liquefy), the oligonucleotide may be released from the particle.

The particle is a microparticle in certain aspects of the invention. The particle may be of any of a wide variety of types; as discussed, the particle may be used to introduce a particular oligonucleotide into a droplet, and any suitable particle to which oligonucleotides can associate with (e.g., physically or chemically) may be used. The exact form of the particle is not critical. The particle may be spherical or non-spherical, and may be formed of any suitable material. In some cases, a plurality of particles is used, which have substantially the same composition and/or substantially the same average diameter. The "average diameter" of a plurality or series of particles is the arithmetic average of the average diameters of each of the particles. Those of ordinary skill in the art will be able to determine the average diameter (or other characteristic dimension) of a plurality or series of particles, for example, using laser light scattering, microscopic examination, or other known techniques. The average diameter of a single particle, in a non-spherical particle, is the diameter of a perfect sphere having the same volume as the non-spherical particle. The average diameter of a particle (and/or of a plurality or series of particles) may be, for example, less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers in some cases. The average diameter may also be at least about 1 micrometer, at least about 2 micrometers, at least about 3 micrometers, at least about 5 micrometers, at least about 10 micrometers, at least about 15 micrometers, or at least about 20 micrometers in certain cases.

The particle may be, in one set of embodiments, a hydrogel particle. See, e.g., Int. Pat. Apl. Pub. No. WO 2008/109176, entitled "Assay and other reactions involving droplets" (incorporated herein by reference) for examples of hydrogel particles, including hydrogel particles containing DNA. Examples of hydrogels include, but are not limited to agarose or acrylamide-based gels, such as polyacrylamide, poly-N-isopropylacrylamide, or poly N-isopropylpolyacrylamide. For example, an aqueous solution of a monomer may be dispersed in a droplet, and then polymerized, e.g., to form a gel. Another example is a hydrogel, such as alginic acid that can be gelled by the addition of calcium ions. In some cases, gelation initiators (ammonium persulfate and TEMED for acrylamide, or Ca for alginate) can be added to a droplet, for example, by co-flow with the aqueous phase, by co-flow through the oil phase, or by coalescence of two different drops, e.g., as discussed in U.S. patent application Ser. No. 11/360,845, filed Feb. 23, 2006, entitled "Electronic Control of Fluidic Species," by Link, et al., published as U.S. Patent Application Publication No. 2007/000342 on Jan. 4, 2007; or in U.S. patent application Ser. No. 11/698,298, filed Jan. 24, 2007, entitled "Fluidic Droplet Coalescence," by Ahn, et al.; each incorporated herein by reference in their entireties.

In another set of embodiments, the particles may comprise one or more polymers. Exemplary polymers include, but are not limited to, polystyrene (PS), polycaprolactone (PCL), polyisoprene (PIP), poly(lactic acid), polyethylene, polypropylene, polyacrylonitrile, polyimide, polyamide, and/or mixtures and/or co-polymers of these and/or other polymers. In addition, in some cases, the particles may be magnetic, which could allow for the magnetic manipulation of the particles. For example, the particles may comprise iron or other magnetic materials. The particles could also be functionalized so that they could have other molecules attached, such as proteins, nucleic acids or small molecules. Thus, some embodiments of the present invention are directed to a set of particles defining a library of, for example, nucleic acids, proteins, small molecules, or other species such as those described herein. In some embodiments, the particle may be fluorescent.

In some aspects, particles such as those discussed herein containing oligonucleotides may be contained within a droplet and the oligonucleotides released from the particle into the interior of the droplet. The droplet may also contain nucleic acid (e.g., produced by lysing a cell), which can be bound to or recognized by the oligonucleotides. The particles and the cells may be introduced within the droplets during and/or after formation of the droplets, and may be added simultaneously or sequentially (in any suitable order). As mentioned, in some embodiments, the particles and the cells may be placed within droplets such that the droplets typically would contain, on average, no more than one particle and no more than one cell.

In one set of embodiments, droplets are formed containing a cell or other source of nucleic acid, and a particle, e.g., comprising an oligonucleotide as described above. Any suitable method may be chosen to create droplets, and a wide variety of different techniques for forming droplets will be known to those of ordinary skill in the art. For example, a junction of channels may be used to create the droplets. The junction may be, for instance, a T-junction, a Y-junction, a channel-within-a-channel junction (e.g., in a coaxial arrangement, or comprising an inner channel and an outer channel surrounding at least a portion of the inner channel), a cross (or "X") junction, a flow-focusing junction, or any other suitable junction for creating droplets. See, for example, International Patent Application No. PCT/US2004/010903, filed Apr. 9, 2004, entitled "Formation and Control of Fluidic Species," by Link, et al., published as WO 2004/091763 on Oct. 28, 2004, or International Patent Application No. PCT/US2003/020542, filed Jun. 30, 2003, entitled "Method and Apparatus for Fluid Dispersion," by Stone, et al., published as WO 2004/002627 on Jan. 8, 2004, each of which is incorporated herein by reference in its entirety. In some embodiments, the junction may be configured and arranged to produce substantially monodisperse droplets. The droplets may also be created on the fluidic device, and/or the droplets may be created separately then brought to the device.

If cells are used, the cells may arise from any suitable source. For instance, the cells may be any cells for which nucleic acid from the cells is desired to be studied or sequenced, etc., and may include one, or more than one, cell type. The cells may be for example, from a specific population of cells, such as from a certain organ or tissue (e.g., cardiac cells, immune cells, muscle cells, cancer cells, etc.), cells from a specific individual or species (e.g., human cells, mouse cells, bacteria, etc.), cells from different organisms, cells from a naturally-occurring sample (e.g., pond water, soil, etc.), or the like. In some cases, the cells may be dissociated from tissue.

In addition, certain embodiments of the invention involve the use of droplets or other discrete compartments, for example, microwells of a microwell plate, individual spots on a slide or other surface, or the like. In some cases, each of the compartments may be in a specific location that will not be accidentally mixed with other compartments. The compartments may be relatively small in some cases, for example, each compartment may have a volume of less than about 1 ml, less than about 300 microliters, less than about 100 microliters, less than about 30 microliters, less than about 10 microliters, less than about 3 microliters, less than about 1 microliter, less than about 500 nl, less than about 300 nl, less than about 100 nl, less than about 50 nl, less than about 30 nl, or less than about 10 nl.

In one set of embodiments, the droplets (or other compartments) are loaded such that, on the average, each droplet has less than 1 particle in it. For example, the average loading rate may be less than about 1 particle/droplet, less than about 0.9 particles/droplet, less than about 0.8 particles/droplet, less than about 0.7 particles/droplet, less than about 0.6 particles/droplet, less than about 0.5 particles/droplet, less than about 0.4 particles/droplet, less than about 0.3 particles/droplet, less than about 0.2 particles/droplet, less than about 0.1 particles/droplet, less than about 0.05 particles/droplet, less than about 0.03 particles/droplet, less than about 0.02 particles/droplet, or less than about 0.01 particles/droplet. In some cases, lower particle loading rates may be chosen to minimize the probability that a droplet will be produced having two or more particles in it. Thus, for example, at least about 50%, at least about 60%, at least about 70%, at least about 80%, at least about 90%, at least about 95%, at least about 97%, at least about 98%, or at least about 99% of the droplets may contain either no particle or only one particle.

Similarly, in some embodiments, the droplets (or other compartments) are loaded such that, on the average, each droplet has less than 1 cell in it. For example, the average loading rate may be less than about 1 cell/droplet, less than about 0.9 cells/droplet, less than about 0.8 cells/droplet, less than about 0.7 cells/droplet, less than about 0.6 cells/droplet, less than about 0.5 cells/droplet, less than about 0.4 cells/droplet, less than about 0.3 cells/droplet, less than about 0.2 cells/droplet, less than about 0.1 cells/droplet, less than about 0.05 cells/droplet, less than about 0.03 cells/droplet, less than about 0.02 cells/droplet, or less than about 0.01 cells/droplet. In some cases, lower cell loading rates may be chosen to minimize the probability that a droplet will be produced having two or more cells in it. Thus, for example, at least about 50%, at least about 60%, at least about 70%, at least about 80%, at least about 90%, at least about 95%, at least about 97%, at least about 98%, or at least about 99% of the droplets may contain either no cell or only one cell. In addition, it should be noted that the average rate of particle loading and the average rate of cell loading within the droplets may the same or different.

In some cases, a relatively large number of droplets may be created, e.g., at least about 10, at least about 30, at least about 50, at least about 100, at least about 300, at least about 500, at least about 1,000, at least about 3,000, at least about 5,000, at least about 10,000, at least about 30,000, at least about 50,000, at least about 100,000 droplets, etc. In some cases, as previously discussed, some or all of the droplets may be distinguishable, e.g., on the basis of the oligonucleotides present in at least some of the droplets (e.g., which may comprise one or more unique sequences or barcodes). In some cases, at least about 50%, at least about 60%, at least about 70%, at least about 80%, at least about 90%, at least about 95%, at least about 97%, at least about 98%, or at least about 99% of the droplets may be distinguishable.

After loading of the particles and cells into droplets, the oligonucleotides may be released or cleaved from the particles, in accordance with certain aspects of the invention. As noted above, any suitable technique may be used to release the oligonucleotides from the droplets, such as light (e.g., if the oligonucleotide includes a photocleavable linker), a chemical, or an enzyme, etc. If a chemical or an enzyme is used, the chemical or enzyme may be introduced into the droplet after formation of the droplet, e.g., through picoinjection or other methods such as those discussed in Int. Pat. Apl. Pub. No. WO 2010/151776, entitled “Fluid Injection” (incorporated herein by reference), through fusion of the droplets with droplets containing the chemical or enzyme, or through other techniques known to those of ordinary skill in the art.

As discussed, in certain aspects, the particles containing oligonucleotides may be used to analyze nucleic acid, for example, arising from a cell, or from other suitable sources. In one set of embodiments, if cells are present, the cells may be lysed within the droplets, e.g., to release DNA and/or RNA from the cell, and/or to produce a cell lysate within the droplet. For instance, the cells may be lysed via exposure to a lysing chemical or a cell lysis reagent (e.g., a surfactant such as Triton-X or SDS, an enzyme such as lysozyme, lysostaphin, zymolase, cellulase, mutanolysin, glycanases, proteases, mannase, proteinase K, etc.), or a physical condition (e.g., ultrasound, ultraviolet light, mechanical agitation, etc.). If a lysing chemical is used, the lysing chemical may be introduced into the droplet after formation of the droplet, e.g., through picoinjection or other methods such as those discussed in U.S. patent application Ser. No. 13/379,782, filed Dec. 21, 2011, entitled “Fluid Injection,” published as U.S. Pat. Apl. Pub. No. 2012/0132288 on May 31, 2012, incorporated herein by reference in its entirety, through fusion of the droplets with droplets containing the chemical or enzyme, or through other techniques known to those of ordinary skill in the art. Lysing of the cells may occur before, during, or after release of the oligonucleotides from the particles. In some cases, lysing a cell will cause the cell to release its contents, e.g., cellular nucleic acids, proteins, enzymes, sugars, etc. In some embodiments, some of the cellular nucleic acids may also be joined to one or more oligonucleotides contained within the droplet, e.g., as discussed herein. For example, in one set of embodiments, RNA transcripts typically produced within the cells may be released and then joined to the oligonucleotides.

In some embodiments, once released, the released nucleic acids from the cell (e.g., DNA and/or RNA) may be bonded to the oligonucleotides, e.g., covalently, through primer extension, through ligation, or the like. Any of a wide variety of different techniques may be used, and those of ordinary skill in the art will be aware of many such techniques. The exact joining technique used is not necessarily critical, and can vary between embodiments.

For instance, in certain embodiments, the nucleic acids may be joined with the oligonucleotides using ligases. Non-limiting examples of ligases include DNA ligases such as DNA Ligase I, DNA Ligase II, DNA Ligase III, DNA Ligase IV, T4 DNA ligase, T7 DNA ligase, T3 DNA Ligase, *E. coli* DNA Ligase, Taq DNA Ligase, or the like. Many such ligases may be purchased commercially. As additional examples, in some embodiments, two or more nucleic acids may be ligated together using annealing or a primer extension method.

In yet another set of embodiments, the nucleic acids may be joined with the oligonucleotides and/or amplified using PCR (polymerase chain reaction) or other suitable amplification techniques, including any of those recited herein. Typically, in PCR reactions, the nucleic acids are heated to cause dissociation of the nucleic acids into single strands, and a heat-stable DNA polymerase (such as Taq polymerase) is used to amplify the nucleic acid. This process is often repeated multiple times to amplify the nucleic acids.

In one set of embodiments, PCR or nucleic acid amplification may be performed within the droplets. For example, the droplets may contain a polymerase (such as Taq polymerase), and DNA nucleotides, and the droplets may be processed (e.g., via repeated heated and cooling) to amplify the nucleic acid within the droplets. The polymerase and nucleotides may be added at any suitable point, e.g., before, during, or after various nucleic acids encoding various conditions are added to the droplets. For instance, a droplet may contain polymerase and DNA nucleotides, which is fused to the droplet to allow amplification to occur. Those of ordinary skill in the art will be aware of suitable PCR techniques and variations, such as assembly PCR or polymerase cycling assembly, which may be used in some embodiments to produce an amplified nucleic acid. Non-limiting examples of such procedures are also discussed below. In addition, in some cases, suitable primers may be used to initiate polymerization, e.g., P5 and P7, or other primers known to those of ordinary skill in the art. In some embodiments, primers may be added to the droplets, or the primers may be present on one or more of the nucleic acids within the droplets. Those of ordinary skill in the art will be aware of suitable primers, many of which can be readily obtained commercially.

In some cases, the droplets may be burst, broken, or otherwise disrupted. A wide variety of methods for "breaking" or "bursting" droplets are available to those of ordinary skill in the art, and the exact method chosen is not critical. For example, droplets contained in a carrying fluid may be disrupted using techniques such as mechanical disruption or ultrasound. Droplets may also be disrupted using chemical agents or surfactants, for example, 1H,1H,2H,2H-perfluorooctanol.

Nucleic acids (labeled with oligonucleotides) from different droplets may then be pooled or combined together or analyzed, e.g., sequenced, amplified, etc. The nucleic acids from different droplets, may however, remain distinguishable due to the presence of different oligonucleotides (e.g., containing different barcodes) that were present in each droplet prior to disruption.

For example, the nucleic acids may be amplified using PCR (polymerase chain reaction) or other amplification techniques. Typically, in PCR reactions, the nucleic acids are heated to cause dissociation of the nucleic acids into single strands, and a heat-stable DNA polymerase (such as Taq polymerase) is used to amplify the nucleic acid. This process is often repeated multiple times to amplify the nucleic acids.

In one set of embodiments, the PCR may be used to amplify the nucleic acids. Those of ordinary skill in the art will be aware of suitable PCR techniques and variations, such as assembly PCR or polymerase cycling assembly, which may be used in some embodiments to produce an amplified nucleic acid. Non-limiting examples of such procedures are also discussed below. In addition, in some cases, suitable primers may be used to initiate polymerization, e.g., P5 and P7, or other primers known to those of ordinary skill in the art. Those of ordinary skill in the art will be aware of suitable primers, many of which can be readily obtained commercially.

Other non-limiting examples of amplification methods known to those of ordinary skill in the art that may be used include, but are not limited to, reverse transcriptase (RT) PCR amplification, in vitro transcription amplification (IVT), multiple displacement amplification (MDA), or quantitative real-time PCR (aPCR).

In some embodiments, the nucleic acids may be sequenced using a variety of techniques and instruments, many of which are readily available commercially. Examples of such techniques include, but are not limited to, chain-termination sequencing, sequencing-by-hybridization, Maxam-Gilbert sequencing, dye-terminator sequencing, chain-termination methods, Massively Parallel Signature Sequencing (Lynx Therapeutics), polony sequencing, pyrosequencing, sequencing by ligation, ion semiconductor sequencing, DNA nanoball sequencing, single-molecule real-time sequencing, nanopore sequencing, microfluidic Sanger sequencing, digital RNA sequencing ("digital RNA-seq"), etc. The exact sequencing method chosen is not critical.

In addition, in some cases, the droplets may also contain one or more DNA-tagged antibodies, e.g., to determine proteins in the cell, e.g., by suitable tagging with DNA. Thus, for example, a protein may be detected in a plurality of cells as discussed herein, using DNA-tagged antibodies specific for the protein.

Additional details regarding systems and methods for manipulating droplets in a microfluidic system in accordance with various aspects of the invention follow, e.g., for determining droplets (or species within droplets), sorting droplets, etc. For example, various systems and methods for screening and/or sorting droplets are described in U.S. patent application Ser. No. 11/360,845, filed Feb. 23, 2006, entitled "Electronic Control of Fluidic Species," by Link, et al., published as U.S. Patent Application Publication No. 2007/000342 on Jan. 4, 2007, incorporated herein by reference. As a non-limiting example, by applying (or removing) a first electric field (or a portion thereof), a droplet may be directed to a first region or channel; by applying (or removing) a second electric field to the device (or a portion thereof), the droplet may be directed to a second region or channel; by applying a third electric field to the device (or a portion thereof), the droplet may be directed to a third region or channel; etc., where the electric fields may differ in some way, for example, in intensity, direction, frequency, duration, etc.

In certain embodiments of the invention, sensors are provided that can sense and/or determine one or more characteristics of the fluidic droplets, and/or a characteristic of a portion of the fluidic system containing the fluidic droplet (e.g., the liquid surrounding the fluidic droplet) in such a manner as to allow the determination of one or more characteristics of the fluidic droplets. Characteristics determinable with respect to the droplet and usable in the invention can be identified by those of ordinary skill in the art. Non-limiting examples of such characteristics include fluorescence, spectroscopy (e.g., optical, infrared, ultraviolet, etc.), radioactivity, mass, volume, density, temperature, viscosity, pH, concentration of a substance, such as a biological substance (e.g., a protein, a nucleic acid, etc.), or the like.

In some cases, the sensor may be connected to a processor, which in turn, cause an operation to be performed on the fluidic droplet, for example, by sorting the droplet, adding or removing electric charge from the droplet, fusing the droplet with another droplet, splitting the droplet, causing mixing to occur within the droplet, etc., for example, as previously described. For instance, in response to a sensor measurement of a fluidic droplet, a processor may cause the fluidic droplet to be split, merged with a second fluidic droplet, etc.

One or more sensors and/or processors may be positioned to be in sensing communication with the fluidic droplet. "Sensing communication," as used herein, means that the sensor may be positioned anywhere such that the fluidic droplet within the fluidic system (e.g., within a channel), and/or a portion of the fluidic system containing the fluidic droplet may be sensed and/or determined in some fashion. For example, the sensor may be in sensing communication with the fluidic droplet and/or the portion of the fluidic system containing the fluidic droplet fluidly, optically or visually, thermally, pneumatically, electronically, or the like. The sensor can be positioned proximate the fluidic system, for example, embedded within or integrally connected to a wall of a channel, or positioned separately from the fluidic system but with physical, electrical, and/or optical communication with the fluidic system so as to be able to sense and/or determine the fluidic droplet and/or a portion of the fluidic system containing the fluidic droplet (e.g., a channel or a microchannel, a liquid containing the fluidic droplet, etc.). For example, a sensor may be free of any physical connection with a channel containing a droplet, but may be positioned so as to detect electromagnetic radiation arising from the droplet or the fluidic system, such as infrared, ultraviolet, or visible light. The electromagnetic radiation may be produced by the droplet, and/or may arise from other portions of the fluidic system (or externally of the fluidic system) and interact with the fluidic droplet and/or the portion of the fluidic system containing the fluidic droplet in such as a manner as to indicate one or more characteristics of the fluidic droplet, for example, through absorption, reflection, diffraction, refraction, fluorescence, phosphorescence, changes in polarity, phase changes, changes with respect to time, etc. As an example, a laser may be directed towards the fluidic droplet and/or the liquid surrounding the fluidic droplet, and the fluorescence of the fluidic droplet and/or the surrounding liquid may be determined. "Sensing communication," as used herein may also be direct or indirect. As an example, light from the fluidic droplet may be directed to a sensor, or directed first through a fiber optic system, a waveguide, etc., before being directed to a sensor.

Non-limiting examples of sensors useful in the invention include optical or electromagnetically-based systems. For example, the sensor may be a fluorescence sensor (e.g., stimulated by a laser), a microscopy system (which may include a camera or other recording device), or the like. As another example, the sensor may be an electronic sensor, e.g., a sensor able to determine an electric field or other electrical characteristic. For example, the sensor may detect capacitance, inductance, etc., of a fluidic droplet and/or the portion of the fluidic system containing the fluidic droplet.

As used herein, a "processor" or a "microprocessor" is any component or device able to receive a signal from one or more sensors, store the signal, and/or direct one or more responses (e.g., as described above), for example, by using a mathematical formula or an electronic or computational circuit. The signal may be any suitable signal indicative of the environmental factor determined by the sensor, for example a pneumatic signal, an electronic signal, an optical signal, a mechanical signal, etc.

In one set of embodiments, a fluidic droplet may be directed by creating an electric charge and/or an electric dipole on the droplet, and steering the droplet using an applied electric field, which may be an AC field, a DC field, etc. As an example, an electric field may be selectively applied and removed (or a different electric field may be applied, e.g., a reversed electric field) as needed to direct the fluidic droplet to a particular region. The electric field may be selectively applied and removed as needed, in some embodiments, without substantially altering the flow of the liquid containing the fluidic droplet. For example, a liquid may flow on a substantially steady-state basis (i.e., the average flowrate of the liquid containing the fluidic droplet deviates by less than 20% or less than 15% of the steady-state flow or the expected value of the flow of liquid with respect to time, and in some cases, the average flowrate may deviate less than 10% or less than 5%) or other predetermined basis through a fluidic system of the invention (e.g., through a channel or a microchannel), and fluidic droplets contained within the liquid may be directed to various regions, e.g., using an electric field, without substantially altering the flow of the liquid through the fluidic system.

In some embodiments, the fluidic droplets may be screened or sorted within a fluidic system of the invention by altering the flow of the liquid containing the droplets. For instance, in one set of embodiments, a fluidic droplet may be steered or sorted by directing the liquid surrounding the fluidic droplet into a first channel, a second channel, etc.

In another set of embodiments, pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Pressure within one or more of the optional downstream flow channels can be controlled to direct the droplet selectively into one of the channels, and changes in pressure can be effected on the order of the time required for successive droplets to reach the junction, such that the downstream flow path of each successive droplet can be independently controlled. In one arrangement, the expansion and/or contraction of liquid reservoirs may be used to steer or sort a fluidic droplet into a channel, e.g., by causing directed movement of the liquid containing the fluidic droplet. The liquid reservoirs may be positioned such that, when activated, the movement of liquid caused by the activated reservoirs causes the liquid to flow in a preferred direction, carrying the fluidic droplet in that preferred direction. For instance, the expansion of a liquid reservoir may cause a flow of liquid towards the reservoir, while the contraction of a liquid reservoir may cause a flow of liquid away from the reservoir. In some cases, the expansion and/or contraction of the liquid reservoir may be combined with other flow-controlling devices and methods, e.g., as described herein. Non-limiting examples of devices able to cause the expansion and/or contraction of a liquid reservoir include pistons and piezoelectric components. In some cases, piezoelectric components may be particularly useful due to their relatively rapid response times, e.g., in response to an electrical signal. In some embodiments, the fluidic droplets may be sorted into more than two channels.

As mentioned, certain embodiments are generally directed to systems and methods for sorting fluidic droplets in a liquid, and in some cases, at relatively high rates. For example, a property of a droplet may be sensed and/or determined in some fashion (e.g., as further described herein), then the droplet may be directed towards a particular region of the device, such as a microfluidic channel, for example, for sorting purposes. In some cases, high sorting speeds may be achievable using certain systems and methods of the invention. For instance, at least about 10 droplets per second may be determined and/or sorted in some cases, and in other cases, at least about 20 droplets per second, at least about 30 droplets per second, at least about 100 droplets per second, at least about 200 droplets per second, at least about 300 droplets per second, at least about 500 droplets per second, at least about 750 droplets per second, at least about 1,000 droplets per second, at least about 1,500 droplets per second, at least about 2,000 droplets per second, at least about 3,000 droplets per second, at least about 5,000 droplets per second, at least about 7,500 droplets per second, at least about 10,000 droplets per second, at least about 15,000 droplets per second, at least about 20,000 droplets per second, at least about 30,000 droplets per second, at least about 50,000 droplets per second, at least about 75,000 droplets per second, at least about 100,000 droplets per second, at least about 150,000 droplets per second, at least about 200,000 droplets per second, at least about 300,000 droplets per second, at least about 500,000 droplets per second, at least about 750,000 droplets per second, at least about 1,000,000 droplets per second, at least about 1,500,000 droplets per second, at least about 2,000,000 or more droplets per second, or at least about 3,000,000 or more droplets per second may be determined and/or sorted.

In some aspects, a population of relatively small droplets may be used. In certain embodiments, as non-limiting examples, the average diameter of the droplets may be less than about 1 mm, less than about 500 micrometers, less than about 300 micrometers, less than about 200 micrometers, less than about 100 micrometers, less than about 75 micrometers, less than about 50 micrometers, less than about 30 micrometers, less than about 25 micrometers, less than about 20 micrometers, less than about 15 micrometers, less than about 10 micrometers, less than about 5 micrometers, less than about 3 micrometers, less than about 2 micrometers, less than about 1 micrometer, less than about 500 nm, less than about 300 nm, less than about 100 nm, or less than about 50 nm. The average diameter of the droplets may also be at least about 30 nm, at least about 50 nm, at least about 100 nm, at least about 300 nm, at least about 500 nm, at least about 1 micrometer, at least about 2 micrometers, at least about 3 micrometers, at least about 5 micrometers, at least about 10 micrometers, at least about 15 micrometers, or at least about 20 micrometers in certain cases. The "average diameter" of a population of droplets is the arithmetic average of the diameters of the droplets.

In some embodiments, the droplets may be of substantially the same shape and/or size (i.e., "monodisperse"), or of different shapes and/or sizes, depending on the particular application. In some cases, the droplets may have a homogenous distribution of cross-sectional diameters, i.e., the droplets may have a distribution of diameters such that no more than about 5%, no more than about 2%, or no more than about 1% of the droplets have a diameter less than about 90% (or less than about 95%, or less than about 99%) and/or greater than about 110% (or greater than about 105%, or greater than about 101%) of the overall average diameter of the plurality of droplets. Some techniques for producing homogenous distributions of cross-sectional diameters of droplets are disclosed in International Patent Application No. PCT/US2004/010903, filed Apr. 9, 2004, entitled "Formation and Control of Fluidic Species," by Link et al., published as WO 2004/091763 on Oct. 28, 2004, incorporated herein by reference.

Those of ordinary skill in the art will be able to determine the average diameter of a population of droplets, for example, using laser light scattering or other known techniques. The droplets so formed can be spherical, or non-spherical in certain cases. The diameter of a droplet, in a non-spherical droplet, may be taken as the diameter of a perfect mathematical sphere having the same volume as the non-spherical droplet.

In some embodiments, one or more droplets may be created within a channel by creating an electric charge on a fluid surrounded by a liquid, which may cause the fluid to separate into individual droplets within the liquid. In some embodiments, an electric field may be applied to the fluid to cause droplet formation to occur. The fluid can be present as a series of individual charged and/or electrically inducible droplets within the liquid. Electric charge may be created in the fluid within the liquid using any suitable technique, for example, by placing the fluid within an electric field (which may be AC, DC, etc.), and/or causing a reaction to occur that causes the fluid to have an electric charge.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. Techniques for producing a suitable electric field (which may be AC, DC, etc.) are known to those of ordinary skill in the art. For example, in one embodiment, an electric field is produced by applying voltage across a pair of electrodes, which may be positioned proximate a channel such that at least a portion of the electric field interacts with the channel. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof.

In another set of embodiments, droplets of fluid can be created from a fluid surrounded by a liquid within a channel by altering the channel dimensions in a manner that is able to induce the fluid to form individual droplets. The channel may, for example, be a channel that expands relative to the direction of flow, e.g., such that the fluid does not adhere to the channel walls and forms individual droplets instead, or a channel that narrows relative to the direction of flow, e.g., such that the fluid is forced to coalesce into individual droplets. In some cases, the channel dimensions may be altered with respect to time (for example, mechanically or electromechanically, pneumatically, etc.) in such a manner as to cause the formation of individual droplets to occur. For example, the channel may be mechanically contracted ("squeezed") to cause droplet formation, or a fluid stream may be mechanically disrupted to cause droplet formation, for example, through the use of moving baffles, rotating blades, or the like. Other techniques of creating droplets include, for example mixing or vortexing of a fluid.

Certain embodiments are generally directed to systems and methods for splitting a droplet into two or more droplets. For example, a droplet can be split using an applied electric field. The droplet may have a greater electrical conductivity than the surrounding liquid, and, in some cases, the droplet may be neutrally charged. In certain embodiments, in an applied electric field, electric charge may be urged to migrate from the interior of the droplet to the surface to be distributed thereon, which may thereby cancel the electric field experienced in the interior of the droplet. In some embodiments, the electric charge on the surface of the droplet may also experience a force due to the applied electric field, which causes charges having opposite polarities to migrate in opposite directions. The charge migration may, in some cases, cause the drop to be pulled apart into two separate droplets.

Some embodiments of the invention generally relate to systems and methods for fusing or coalescing two or more droplets into one droplet, e.g., where the two or more droplets ordinarily are unable to fuse or coalesce, for example, due to composition, surface tension, droplet size, the presence or absence of surfactants, etc. In certain cases, the surface tension of the droplets, relative to the size of the droplets, may also prevent fusion or coalescence of the droplets from occurring.

As a non-limiting example, two droplets can be given opposite electric charges (i.e., positive and negative charges, not necessarily of the same magnitude), which can increase the electrical interaction of the two droplets such that fusion or coalescence of the droplets can occur due to their opposite electric charges. For instance, an electric field may be applied to the droplets, the droplets may be passed through a capacitor, a chemical reaction may cause the droplets to become charged, etc. The droplets, in some cases, may not be able to fuse even if a surfactant is applied to lower the surface tension of the droplets. However, if the droplets are electrically charged with opposite charges (which can be, but are not necessarily of, the same magnitude), the droplets may be able to fuse or coalesce. As another example, the droplets may not necessarily be given opposite electric charges (and, in some cases, may not be given any electric charge), and are fused through the use of dipoles induced in the droplets that causes the droplets to coalesce. Also, the two or more droplets allowed to coalesce are not necessarily required to meet "head-on." Any angle of contact, so long as at least some fusion of the droplets initially occurs, is sufficient. See also, e.g., U.S. patent application Ser. No. 11/698,298, filed Jan. 24, 2007, entitled "Fluidic Droplet Coalescence," by Ahn, et al., published as U.S. Patent Application Publication No. 2007/0195127 on Aug. 23, 2007, incorporated herein by reference in its entirety.

In one set of embodiments, a fluid may be injected into a droplet. The fluid may be microinjected into the droplet in some cases, e.g., using a microneedle or other such device. In other cases, the fluid may be injected directly into a droplet using a fluidic channel as the droplet comes into contact with the fluidic channel. Other techniques of fluid injection are disclosed in, e.g., International Patent Application No. PCT/US2010/040006, filed Jun. 25, 2010, entitled "Fluid Injection," by Weitz, et al., published as WO 2010/151776 on Dec. 29, 2010; or International Patent Application No. PCT/US2009/006649, filed Dec. 18, 2009, entitled "Particle-Assisted Nucleic Acid Sequencing," by Weitz, et al., published as WO 2010/080134 on Jul. 15, 2010, each incorporated herein by reference in its entirety.

A variety of materials and methods, according to certain aspects of the invention, can be used to form articles or components such as those described herein, e.g., channels such as microfluidic channels, chambers, etc. For example, various articles or components can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, Scientific American, 248:44-55, 1983 (Angell, et al).

In one set of embodiments, various structures or components of the articles described herein can be formed of a polymer, for example, an elastomeric polymer such as polydimethylsiloxane ("PDMS"), polytetrafluoroethylene ("PTFE" or TEFLON®), or the like. For instance, according to one embodiment, a microfluidic channel may be implemented by fabricating the fluidic system separately using PDMS or other soft lithography techniques (details of soft lithography techniques suitable for this embodiment are discussed in the references entitled "Soft Lithography," by Younan Xia and George M. Whitesides, published in the *Annual Review of Material Science,* 1998, Vol. 28, pages 153-184, and "Soft Lithography in Biology and Biochemistry," by George M. Whitesides, Emanuele Ostuni, Shuichi Takayama, Xingyu Jiang and Donald E. Ingber, published in the *Annual Review of Biomedical Engineering,* 2001, Vol. 3, pages 335-373; each of these references is incorporated herein by reference).

Other examples of potentially suitable polymers include, but are not limited to, polyethylene terephthalate (PET), polyacrylate, polymethacrylate, polycarbonate, polystyrene, polyethylene, polypropylene, polyvinylchloride, cyclic olefin copolymer (COC), polytetrafluoroethylene, a fluorinated polymer, a silicone such as polydimethylsiloxane, polyvinylidene chloride, bis-benzocyclobutene ("BCB"), a polyimide, a fluorinated derivative of a polyimide, or the like. Combinations, copolymers, or blends involving polymers including those described above are also envisioned. The device may also be formed from composite materials, for example, a composite of a polymer and a semiconductor material.

In some embodiments, various structures or components of the article are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, waxes, metals, or mixtures or composites thereof heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, dodecyltrichlorosilanes, etc.

Silicone polymers are used in certain embodiments, for example, the silicone elastomer polydimethylsiloxane. Non-limiting examples of PDMS polymers include those sold under the trademark Sylgard by Dow Chemical Co., Midland, MI, and particularly Sylgard 182, Sylgard 184, and Sylgard 186. Silicone polymers including PDMS have several beneficial properties simplifying fabrication of various structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures or channels from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, structures can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," *Anal. Chem.,* 70:474-480, 1998 (Duffy et al.), incorporated herein by reference.

Thus, in certain embodiments, the design and/or fabrication of the article may be relatively simple, e.g., by using relatively well-known soft lithography and other techniques such as those described herein. In addition, in some embodiments, rapid and/or customized design of the article is possible, for example, in terms of geometry. In one set of embodiments, the article may be produced to be disposable, for example, in embodiments where the article is used with substances that are radioactive, toxic, poisonous, reactive, biohazardous, etc., and/or where the profile of the substance (e.g., the toxicology profile, the radioactivity profile, etc.) is unknown. Another advantage to forming channels or other structures (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

The following documents are each incorporated herein by reference in its entirety for all purposes: U.S. Pat. Apl. Ser. No. 61/980,541, entitled "Methods and Systems for Droplet Tagging and Amplification," by Weitz, et al.; U.S. Pat. Apl. Ser. No. 61/981,123, entitled "Systems and Methods for Droplet Tagging," by Bernstein, et al.; Int. Pat. Apl. Pub. No. WO 2004/091763, entitled "Formation and Control of Fluidic Species," by Link et al.; Int. Pat. Apl. Pub. No. WO 2004/002627, entitled "Method and Apparatus for Fluid Dispersion," by Stone et al.; Int. Pat. Apl. Pub. No. WO 2006/096571, entitled "Method and Apparatus for Forming Multiple Emulsions," by Weitz et al.; Int. Pat. Apl. Pub. No. WO 2005/021151, entitled "Electronic Control of Fluidic Species," by Link et al.; Int. Pat. Apl. Pub. No. WO 2011/056546, entitled "Droplet Creation Techniques," by Weitz, et al.; Int. Pat. Apl. Pub. No. WO 2010/033200, entitled "Creation of Libraries of Droplets and Related Species," by Weitz, et al.; U.S. Pat. Apl. Pub. No. 2012-0132288, entitled "Fluid Injection," by Weitz, et al.; Int. Pat. Apl. Pub. No. WO 2008/109176, entitled "Assay And Other Reactions Involving Droplets," by Agresti, et al.; and Int. Pat. Apl. Pub. No. WO 2010/151776, entitled "Fluid Injection," by Weitz, et al.; and U.S. Pat. Apl. Ser. No. 62/072,944, entitled "Systems and Methods for Barcoding Nucleic Acids," by Weitz, et al.

In addition, the following are incorporated herein by reference in their entireties: U.S. Pat. Apl. Ser. No. 61/981,123 filed Apr. 17, 2014; PCT Pat. Apl. Ser. No. PCT/US2015/026338, filed Apr. 17, 2015, entitled "Systems and Methods for Droplet Tagging"; U.S. Pat. Apl. Ser. No. 61/981,108 filed Apr. 17, 2014; a PCT application filed on Apr. 17, 2015, entitled "Methods and Systems for Droplet Tagging and Amplification"; U.S. Pat. Apl. Ser. No. 62/072,944, filed Oct. 30, 2014; and PCT Pat. Apl. Ser. No. PCT/US2015/026443, filed on Apr. 17, 2015, entitled "Systems and Methods for Barcoding Nucleic Acids."

The following examples are intended to illustrate certain embodiments of the present invention, but do not exemplify the full scope of the invention.

Example 1

The following examples describe various systems and methods for performing high-throughput sequencing within droplets using universal barcoding.

A PCT application, Pat. Apl. Ser. No. PCT/US2015/026443, entitled "Systems and Methods for Barcoding Nucleic Acids," by Weitz, et al., incorporated herein by reference in its entirety, generally describes droplet microfluidics and barcoded hydrogels. Polyacrylamide hydrogels, containing many copies of a DNA that contains a barcode and a poly-dT sequence, can be created in certain embodiments, along with nanoliter droplets to contain one barcoding bead, a single cell, a buffer for cell lysis and reverse transcription, and reverse transcriptase. Single-cell reverse transcription can be performed in droplets so that mRNA transcripts can be converted into barcoded-cDNA. This cDNA can be prepared for high-throughput sequencing. Because the cDNAs may contain a barcode to identify its source cell, sequencing analysis can be performed, for instance, in a single HiSeq run. This allows transcriptional profiling of thousands of individual cells in a single experiment, at an unprecedented level of efficiency in terms of precision, cost and time.

This example illustrates the creation and use of universal barcoding beads. These contain a universal adapter that can accept target-specific DNA oligonucleotides or to a specific PCR product. In this way, a set of universal barcodes can be adapted to specifically recognize any nucleic acid sequence of interest. This has a major impact on the general utility of the methods and may streamline commercialization of the barcoding technique. For example, with this modification, the technically difficult portion of barcoding bead manufacture, the synthesis of the bead with an attached barcode, can be performed with high quality control. Customers can then perform straightforward steps to generate target-specific reagents.

The following examples illustrates a general strategy to encapsulate a library of beads carrying DNA barcodes into droplets, together with individual templates (cells, molecules organelles, or nuclei, or other discrete templates), and also together with gene specific primers. The barcoded beads are generally synthesized as described in U.S. Pat. Apl. Ser. No. 62/072,944. The gene specific primers allow amplification of loci of interest, while the bead-delivered barcoded primers identify the template source of the amplicons.

Example 2

One example method involving amplicon barcoding is as follows. See also FIG. 1.

In this example, a pool of beads is prepared, carrying many copies of a primer with a single barcode, but with at least 100,000 different barcodes across the bead pool. The beads are generally synthesized as described in U.S. Pat. Apl. Ser. No. 62/072,944. However, the 3' end of barcoded primers on the beads can be replaced with a Universal Amplification Sequence. The beads are encapsulated with individual templates (e.g., cells, molecules organelles, or nuclei, or other discrete templates) into picoliter-sized drops with Gene-Specific Reverse Primers and Gene-Specific Inner Forward Primers. The Gene-Specific Inner Forward Primers may contain, at their 5' ends, a sequence that may be complementary to the Universal Amplification Sequence on the DNA barcode.

Two-stage PCR is performed in the droplets. A gene-specific amplicon is generated using gene-specific pairs comprised of a Gene-Specific Inner Forward Primer and a Gene-Specific Reverse Primer. The concentration of the Gene-Specific Inner Forward Primer may be lower than that of the Gene-Specific Reverse primer to ensure that it is substantially consumed during amplification. The 5' terminus of the Forward end of the amplicons produced during PCR will contain the Universal Amplification Sequence. Then, in the second stage of PCR, the barcode DNA can serve as a Universal Outer Forward primer and the amplicons may be further amplified using primer pairs comprised of the bead affixed DNA and the Gene-Specific Reverse Primer. This process incorporates the barcode sequence into the amplicons.

The annealing temperature for the second stage of PCR can be higher than that used for the first stage PCR. This can increase use of the longer, bead affixed DNA as forward primer in the second stage of PCR.

The droplets are then burst to retrieve the bar-coded amplicons, and PCR may be performed to append bases required for Illumina sequencing. Sequencing, e.g., deep sequencing, may then be performed.

Example 3

This example illustrates another method of amplicon barcoding. See also FIGS. 2 and 3. In the previous example, DNA barcodes are added to amplicons of interest by PCR. In this example, one end of the PCR amplicons can be joined to a barcoding bead through, e.g., ligation. In this example, ligation-ready amplicons are produced in droplets, and then these drops are merged to form a library of beads carrying DNA barcodes with a universal sequence can be also created through a drop merging scheme.

The barcoding beads are first prepared. A pool of beads is prepared, carrying many copies of a primer with a single barcode, but with at least 100,000 different barcodes across the bead pool. The beads are synthesized substantially as described in U.S. Pat. Apl. Ser. No. 62/072,944. However, the barcoding DNA molecules can be constructed so that they can be efficiently joined to PCR amplicons of interest.

The free end of the bead-affixed bar-coding DNA may be at least partially double-stranded and may contain an overhanging thymine (T) at the 3' end of one strand. This modification creates an end that can be efficiently joined to PCR amplicons having a single overhanging adenine (A).

The free end of the bead-affixed bar-coding DNA may be at least partially double-stranded and contain overhanging sequence that creates a specific "sticky end." This sticky end may be efficiently joined to DNA fragments that contain the corresponding "complementary" sticky end. For example, the PCR primers used to generate target-specific amplicons may include sequences that encode a particular restriction enzyme site. An amplicon generated with these primers can be cut with a restriction enzyme to leave an end that may be compatible with sticky end on the bar-immobilized barcode.

The free end of the bead-affixed bar-coding DNA may be at least partially single-stranded and contain sequence that joins efficiently to a PCR product with a specific "sticky end" or a PCR product with a single overhanging base.

A variety of enzymes, including but not limited to ligases, topoisomerases, and recombinases may be used to join PCR amplicons to nucleic acid barcodes. A variety of enzymes, including but not limited to kinases, restriction enzymes, Type II S restriction enzymes, and single-strand nickases may be used to prepare the ends of the barcoding DNA and the PCR amplicons for efficient joining. Some strategies may generate sticky ends so that barcodes preferentially ligate to amplicons, amplicons do not ligate to amplicons, and barcodes do not ligate to barcodes. Various molecular biology enzymes and methods can be combined to ensure these preferred combinations.

The templates (e.g., single molecules or cells) can be encapsulated into droplets (e.g., picoliter-sized drops) with template-specific primers and PCR reagents. PCR then can be performed within the droplets. The reverse primers may contain an additional sequence at its 5' end, which encodes an adaptor for use in sequencing, for example, an Illumina sequencing primer. In addition, the PCR primers and PCR conditions may be selected to ensure that the amplicons generated can be efficiently joined to the nucleic acid barcodes.

For example, if the free end of the bead-affixed DNA barcode contains an overhanging thymine (T) at the 3' end of one strand, then one amplicon-specific primer may contain a phosphorylated 5' end. In addition, the PCR enzyme and conditions can append a single non-templated (overhanging) A to the 3' ends of the amplicon. In this way, the amplicon and template may be covalently ligated using, e.g., T4 DNA ligase. This ligated "top strand" can serve as a template for PCR. The 5' strand of the free end of the bead affixed DNA may be dephosphorylated to ensure that a specified end of the amplicon is ligated to the barcoding DNA.

As another example, if the free end of the bead-affixed bar-coding DNA contains overhanging sequence that creates a specific "sticky end," then PCR can be performed with a primer that appends DNA that can be modified to create the complementary sticky end. For example, the PCR primer may add sequence that is recognized and cut a specific restriction enzyme, leaving a DNA end that may be complementary to the end of the barcoding DNA.

After the amplification reaction in the droplets, barcoding hydrogel beads may be added to the drops containing PCR amplicons, e.g., via pico-injection (see, Int. Pat. Apl. Pub. No. WO 2010/151776, published Dec. 29, 2010, entitled "Fluid Injection," by Weitz, et al., incorporated herein by reference in its entirety) or other suitable techniques. The injection also may add reagents to join the amplicon to a DNA barcode. For example, a ligase (or a topoisomerase or a similar enzyme) may join A-tailed PCR amplicon to a T-tailed barcoding DNA; a ligase and an appropriate restriction enzyme (or nickase) may be added if the amplicon end needs modification; and/or kinases or dephosphorylases may be used for molecular biology manipulations.

The merged droplets may be incubated to allow joining of amplicon to barcoding DNA. Then the droplets may be broken and another round of PCR performed to generate a full-length adaptor.

In some cases, to further increase detection of low copy templates, a variety of linear (low-bias) amplification methods may be used. For example, the barcode DNA can contain a T7 promoter sequence to facilitate linear amplification methods using T7 RNA polymerase.

Example 4

In this example, the method shown in FIG. 1A was used to show single-cell targeted gene barcoding-sequencing. Two cell lines were selected. One cell line had an EGFR exon 21 L858R mutation, and the other one carried an EGFR exon 19 deletion. A series of cell mixtures were prepared by mixing two cell lines at ratios of 1:1, 1:10, 1:50 and 0:100. A microfluidic drop-maker was used to co-encapsulate singles cells and lysis buffer into 50 micrometer drops. Then, a microfluidic liquid injector was used to add a PCR mixture containing primers for both exon regions, followed by thermal cycling.

To barcode the amplicons from individual cells, a microfluidic bead injector was used, which had four inlets: the two at the upstream were for drops containing PCR amplicons and spacing oil, and the other two at the downstream were for the injection of beads and PCR mixture. The drops containing amplicons were flowed into a device and spaced into single file using HFE 7500 oil with 1% w/w surfactant. In the downstream portion of the device, barcoded beads and PCR mixture were injected into the drops by electro-coalescence. The flow rates used to inject the drops were chosen to ensure that one barcode gels fuses with a gDNA-bearing drop. The flow rate of the PCR cocktail was chosen to ensure that the buffer is added at ~1:1 ratio upon coalescence. The drops were collected and a second round of in-drop PCR was performed, followed by breaking the drop and adding unique indexes to individual samples through in-bulk PCR which allowed the samples to be sequenced together.

Figure 5:
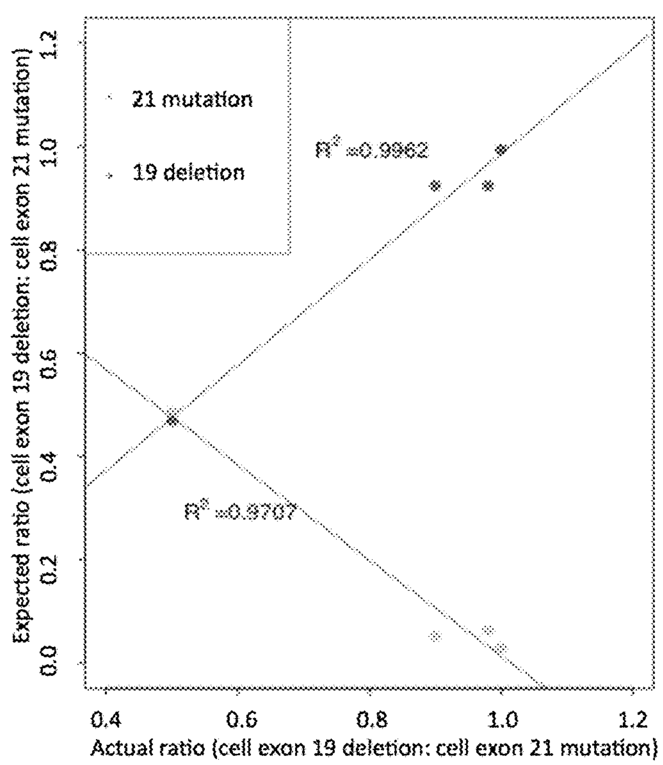
FIG. 5 illustrates the determination of genotypes from cells in accordance with an embodiment of the invention.

After sequencing, data analysis was performed to determine the genotype from each individual cells. The results are shown in FIG. 5. In the cell line that carried exon 19 deletions, an increased ratio was shown. But in the cell line where there was no exon 21 mutation, such that when it was mixed with the cell line carrying the exon 21 mutation, the ratio of mutant exon 21 decreased.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the invention includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:

(a) providing a plurality of droplets comprising particles such that at least about 90% of the droplets contains one particle or no particle, the particles comprising oligonucleotides, the oligonucleotides comprising an adapter sequence that is identical for all of the plurality of droplets and particles, and a first barcode selected from a pre-defined pool of first barcodes, and a second barcode selected from a pre-defined pool of second barcodes, such that substantially each of the particles comprises distinguishable barcode sequences;

(b) encapsulating cells within the plurality of droplets at a density of less than 1 cell/droplet;

(c) lysing at least some of the cells within the plurality of droplets to release nucleic acid from the cells;

(d) attaching a released nucleic acid sequence to the oligonucleotides via covalent bonding after lysing at least some of the cells; and (e) selectively amplifying the attached released nucleic acid sequence by:

(i) exposing the adapter sequence to a gene-specific inner forward primer comprising a sequence complementary to the adapter sequence and a sequence complementary to the released nucleic acid sequence; and (ii) exposing the gene-specific inner forward primer and a gene-specific reverse primer to the released nucleic acid sequence, wherein the concentration of the gene-specific inner forward primer is lower than the concentration of the gene-specific reverse primer;

thereby generating an amplicon, wherein the amplicon is further amplified using the oligonucleotide and the gene-specific reverse primer to produce an oligonucleotide comprising the first barcode, the second barcode, and the amplicon.

2. The method according to claim 1, wherein covalent bonding occurs by enzymatic attachment or ligation.

3. The method according to claim 1, wherein, prior to (d), the oligonucleotides and the released nucleic acid sequence both have sticky ends.

4. The method according to claim 3, wherein the released nucleic acid sequence comprises an overhang region and the oligonucleotides comprise a complementary overhang region, and wherein the overhang region and the complementary overhang region contain a single nucleotide, or a random sequence of nucleotides, or a restriction site.

5. The method according to claim 1, wherein the pre-defined pool of first barcodes comprises at least about 300 distinguishable barcodes.

6. The method according to claim 1, wherein the pre-defined pool of second barcodes comprises at least about 300 distinguishable barcodes.

7. The method according to claim 1, wherein the distinguishable barcode sequences comprise at least 10,000 distinguishable barcode sequences.

8. The method according to claim 1, wherein at least some of the oligonucleotides are attached to the surface of the particles.

9. The method according to claim 1, wherein at least some of the oligonucleotides are covalently bonded to the particles.

10. The method according to claim 1, wherein at least some of the oligonucleotides comprise a cleavable linker.

11. The method according to claim 1, further comprising releasing at least some of the oligonucleotides from the particles prior to lysing at least some of the cells.

12. The method according to claim 1, wherein the particles are contained within the droplets at no more than about 1 particle/droplet.

13. The method according to claim 1, wherein the plurality of droplets further comprise DNA-tagged antibodies.

* * * * *